(12) United States Patent
Khan et al.

(10) Patent No.: US 7,358,330 B2
(45) Date of Patent: *Apr. 15, 2008

(54) IMMUNOREGULATORY COMPOSITIONS

(75) Inventors: Nisar Ahmed Khan, Rotterdam (NL); Robbert Benner, Barendrecht (NL)

(73) Assignee: Biotempt B.V., Koekange (NL)

( * ) Notice: Subject to any disclaimer, the term of this patent is extended or adjusted under 35 U.S.C. 154(b) by 476 days.

This patent is subject to a terminal disclaimer.

(21) Appl. No.: 10/753,510

(22) Filed: Jan. 7, 2004

(65) Prior Publication Data

US 2004/0208885 A1 Oct. 21, 2004

Related U.S. Application Data

(63) Continuation-in-part of application No. 10/028,075, filed on Dec. 21, 2001, and a continuation of application No. 10/262,522, filed on Sep. 30, 2002, which is a continuation of application No. PCT/NL01/00259, filed on Mar. 3, 2001, and a continuation-in-part of application No. PCT/NL02/00639, filed on Apr. 10, 2002.

(51) Int. Cl.
C07K 5/103 (2006.01)
A61K 38/07 (2006.01)

(52) U.S. Cl. .......................... 530/300; 514/2
(58) Field of Classification Search .............. None
See application file for complete search history.

(56) References Cited

U.S. PATENT DOCUMENTS

| | | |
|---|---|---|
| 4,427,660 A | 1/1984 | Schiffman et al. |
| 4,571,336 A | 2/1986 | Houck et al. |
| 4,753,965 A | 6/1988 | Stemerick et al. |
| 4,855,285 A | 8/1989 | Stevens |
| 4,977,244 A | 12/1990 | Muchmore et al. |
| 5,002,961 A | 3/1991 | Dage et al. |
| 5,223,397 A | 6/1993 | Pouletty |
| 5,380,668 A | 1/1995 | Herron |
| 5,677,275 A | 10/1997 | Lunardi-Iskandar et al. |
| 5,801,193 A | 9/1998 | Ojo-Amaize et al. |
| 5,837,478 A * | 11/1998 | Gallatin et al. ............ 435/7.24 |
| 5,851,997 A | 12/1998 | Harris |
| 5,854,004 A | 12/1998 | Czemilofsky et al. |
| 5,856,440 A * | 1/1999 | Wang ........................ 530/334 |
| 5,877,148 A | 3/1999 | Lunardi-Iskandar et al. |
| 5,942,494 A | 8/1999 | Ginsberg et al. |
| 5,958,413 A | 9/1999 | Anagnostopulos et al. |
| 5,968,513 A | 10/1999 | Gallo et al. |
| 5,972,924 A | 10/1999 | Keep et al. |
| 5,981,486 A | 11/1999 | Matsushima et al. |
| 5,994,126 A | 11/1999 | Steinman et al. |
| 5,997,871 A | 12/1999 | Gallo et al. |
| 6,051,596 A | 4/2000 | Badger |
| 6,075,150 A | 6/2000 | Wang et al. |
| 6,150,500 A | 11/2000 | Salerno |
| 6,235,281 B1 | 5/2001 | Stenzel et al. |
| 6,310,041 B1 | 10/2001 | Haddox et al. |
| 6,319,504 B1 | 11/2001 | Gallo et al. |
| 6,361,992 B1 | 3/2002 | Szkudlinski et al. |
| 6,489,296 B1 | 12/2002 | Grinnell et al. |
| 6,583,109 B1 | 6/2003 | Gallo et al. |
| 6,596,688 B1 | 7/2003 | Gallo et al. |
| 6,620,416 B1 | 9/2003 | Gallo et al. |
| 6,630,138 B2 | 10/2003 | Gerlitz et al. |
| 6,727,227 B1 | 4/2004 | Khavinson |
| 6,831,057 B2 | 12/2004 | Baldwin et al. |
| 6,844,315 B2 | 1/2005 | Khan et al. |
| 2002/0041871 A1 | 4/2002 | Brudnak |
| 2002/0064501 A1 | 5/2002 | Khan et al. |
| 2003/0049273 A1 | 3/2003 | Gallo et al. |
| 2003/0113733 A1 | 6/2003 | Khan et al. |
| 2003/0119720 A1 | 6/2003 | Khan et al. |
| 2003/0148955 A1 | 8/2003 | Pluenneke |
| 2003/0166556 A1 | 9/2003 | Khan et al. |
| 2003/0186244 A1 | 10/2003 | Margus et al. |

(Continued)

FOREIGN PATENT DOCUMENTS

| | | |
|---|---|---|
| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| GB | 2 194 886 A | 3/1988 |
| WO | WO 96/04008 | 2/1996 |
| WO | WO 97/49373 | 12/1997 |
| WO | WO 97/49418 | 12/1997 |
| WO | WO 97/49432 | 12/1997 |

(Continued)

OTHER PUBLICATIONS

PCT International Search Report, PCT/NL01/00259, dated Dec. 18, 2001, 3 pages.
PCT International Preliminary Examination Report, PCT/NL99/00313, dated Jul. 21, 2000, 6 pages.

(Continued)

Primary Examiner—Celine Qian
Assistant Examiner—Jennifer Dunston
(74) Attorney, Agent, or Firm—TraskBritt

(57) ABSTRACT

The invention relates to compounds exhibiting immunoregulatory activity as determined by measuring the compound's ability to modulate production of NO by a cell. Preferred compounds include or consist of a sequence

AAL AAQ AAG AAV wherein AAL is a substituted or unsubstituted non-polar amino acid selected from the group consisting of Ala and Leu; wherein AAQ is a substituted or unsubstituted amino acid selected from the group consisting of Gln, Pro, and Ala; wherein AAG is a substituted or unsubstituted amino acid Gly, and wherein AAV is a substituted or unsubstituted non-polar amino acid selected from the group consisting of Val and Ala. In one embodiment, the compound consists of a tripeptide selected from the group AQG, MTR, VVC, and mixtures thereof.

1 Claim, No Drawings

U.S. PATENT DOCUMENTS

| | | |
|---|---|---|
| 2003/0215434 A1 | 11/2003 | Khan et al. |
| 2003/0219425 A1 | 11/2003 | Khan et al. |
| 2003/0220257 A1 | 11/2003 | Benner et al. |
| 2003/0220258 A1 | 11/2003 | Benner et al. |
| 2003/0220259 A1 | 11/2003 | Benner et al. |
| 2003/0220260 A1 | 11/2003 | Khan et al. |
| 2003/0220261 A1 | 11/2003 | Khan et al. |
| 2003/0224995 A1 | 12/2003 | Khan et al. |
| 2004/0013661 A1 | 1/2004 | Wensvoort et al. |
| 2005/0037430 A1 | 2/2005 | Khan et al. |
| 2005/0214943 A1 | 9/2005 | Khan et al. |
| 2005/0227925 A1 | 10/2005 | Benner et al. |
| 2006/0111292 A1 | 5/2006 | Khan et al. |
| 2006/0142205 A1 | 6/2006 | Benner et al. |

FOREIGN PATENT DOCUMENTS

| | | |
|---|---|---|
| WO | WO 97/49721 | 12/1997 |
| WO | WO 98/34631 A1 | 8/1998 |
| WO | WO 98/35691 | 8/1998 |
| WO | WO 99/59617 | 11/1999 |
| WO | WO 01/10907 A2 | 2/2001 |
| WO | WO 01/11048 A2 | 2/2001 |
| WO | WO 01/29067 | 4/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 A2 | 4/2003 |

OTHER PUBLICATIONS

PCT International Search Report, PCT/EP99/00313, dated Nov. 29, 1999, 3 pages.

International Search Report, International Application No. PCT/NL02/00639, mailed Aug. 4, 2003 (8 pages).

Connelly et al., Biphasic Regulation of NF-kB Activity Underlies the Pro- and Anti-Inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Medzhitov, Toll-like Receptors and Innate Immunity, Nature Reviews/Immunology, Nov. 2001, pp. 135-145, vol. 1.

Lang et al., "Induction of apoptosis in Kaposi's sarcoma spindle cell cultures by the subunits of human chorionic gonadotropin", AIDS 1997, vol. 11, No. 11, pp. 1333-1340.

Iskandar et al., "Effects of a urinary factor from women in early pregnancy on HIV-1. SIV and associated disease", Nature Medicine, Apr. 1998, vol. 4, No. 4, pp. 428-434.

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Rohrig et al., Growth-stimulating Influence of Human Chorionic Gonadotropin (hCG) on Plasmodium falciparum in vitro, Zentralblatt Bakt, 1999, pp. 89-99, vol. 289.

Tak et al., NF-kappaB: a key role in inflammatory disease, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-kB in Cytokine Gene Regulation," 17 Am. J. Respir. Cell Mol. Biol. 3-9 (1997).

Keller, S., et al., "Human Chorionic Gonadotropin (hCG) Is a Potent Angiogenic Factor for Uterine Endothelial Cells in Vitro," 20(5-6) PLACENTA, p. A37 (Jul. 1999).

Khan, Nisar A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Patil, A., et al., "The Study of the Effect of Human Chorionic Gonadotrophic (HCG) Hormone on the Survival of Adrenal Medulla Transplant in Brain. Preliminary Study," 87 Acta Neurochir (Wien) 76-78 (1987).

Slater, Lewis M., et al., "Decreased Mortality of Murine Graft-Versus-Host Disease by Human Chorionic gonadotropin,"23(1) TRANSPLANTATION 103-104 (Jan. 1977).

Wulczyn, F. Gregory, et al., "Th NF-kB/Rel and IkB gene families: mediators of immune response and inflammation," 74(12) J. Mol. Med. 749-769 (1996).

Yamamoto, Y., et al., "Role of the Nf-kB Pathway in the Pathogenesis of Human Disease States," 1(3) Current Molecular Medicine 287-296 (Jul. 2001).

Kachra et al., "Low Molecular Weight Components but Not Dimetric HCG Inhibit Growth and Down-Regulate AP-1 Transcription Factor in Kaposi's Sarcoma Cells," Endocrinology, 1997, pp. 4038-4041, vol. 138, No. 9.

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

Abraham, E., "Coagulation Abnormalities in Acute Lung Injury and Sepsis," Am. J. Respir. Cell Mol. Biol., 2000, pp. 401-404, vol. 22.

Adib-Conquy et al., "NF-kappaB Expression in Mononuclear Cells in Patients with Sepsis Resembles That Observed in Lipopolysaccharide Tolerance," Am. J. Respir. Crit. Care Med., 2000, pp. 1877-1883, vol. 162.

Arima et al., "IL-2-Induced Growth of CD8= T Cell Prolymphocytic Leukemia Cells Mediated by NF-kappaB Induction and IL-2 Receptor alpha Expression," Leukemia Research, 1998, pp. 265-273, vol. 22, No. 3.

Baeuerle et al., "Function and Activation of NF-kappaB in the Immune System," Annu. Rev. Immunol., 1994, pp. 141-179, vol. 12.

Bethea et al., "Traumatic Spinal Cord Injury Induces Nuclear Factor-kappaB Activation," The Journal of Neuroscience, May 1, 1998, pp. 3251-3260, vol. 18, No. 9.

Bodfish et al., "Treating the Core Features of Autism: Are We There Yet?" Mental Retardation and Developmental Disabilities Research Reviews, 2004, pp. 318-326, vol. 10.

Brown et al., "Two Forms of NF-kappaB1 (p105/p50) in Murine Macrophages: Differential Regulation by Lipopolysaccharide, Interleukin-2, and Interferon-gamma," Journal of Interferon and Cytokine Research, 1997, pp. 295-306, vol. 17.

Cui et al., Am. J. Physiol. Integr. Comp. Physiol., 2004, pp. R699-R709, vol. 286.

Dwinnell et al., Atlas of Diseases of the Kidney, Blackwell Sciences, 1999, pp. 12.1-12.12, Ch. 12.

Emmel et al., "Cyclosporin A Specifically Inhibits Function of Nuclear Proteins Involved in T Cell Activation," Science, Dec. 22, 1989, pp. 1617-1620.

Epinat et al., "Diverse agents act at mulitple levels to inhibit the Rel/NF-kappaB signal transduction pathway," Oncogene, 1999, pp. 6896-6909, vol. 18.

Faust et al., "Disseminated intravascular coagulation and purpura fulminans secondary to infection," Bailliere's Clinical Haematology, 2000, 179-197, vol. 13. No. 2.

Jimenez-Garza et al., "Early Effects of Modulation Nuclear factor-kappaB Activation on Traumatic Spinal Cord Injury in Rats," Ann. N.Y Acad. Sci., 2005, pp. 148-150, vol. 1053.

Kalns et al., Biochem. Biophys. Res. Comm., 2002, pp. 41-44, vol. 292.

Kalns et al., Biochem. Biophys. Res. Comm., 2002, pp. 506-509, vol. 297.

Kidd et al., "Autism, An Extreme Challenge to Integrative Medicine. Part II: Medical Management," Alternative Medicine Review, 2002, pp. 472-499, vol. 7, No. 6.

Kronfol et al., "Cytokines and the Brain: Implications for Clinical Psychiatry," Am. J. Psychiatry, May 2000, pp. 683-694, vol. 157, No. 5.

Li et al., "NF-kappaB Regulation in the Immune System," Nature Reviews/Immunology, Oct. 2002, pp. 725-734, vol. 2.

Malek-Ahmadi, P., "Role of Cytokines in Psychopathology: Therapeutic Implications," Drug News Prospects, Jun. 1998, pp. 271-276, vol. 11, No. 5.

McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.

McDonald et al., "Interleukin-15 (IL-15) Induced NF-kappaB Activation and IL-8 Production in Human Neutrophils," Blood, Dec. 15, 1998, pp. 4828-4835, vol. 92, No. 12.

Merck Index, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Neely et al., "Then and now: Studies using a burned mouse model reflect trends in burn research over the past 25 years," Burns, 1999, pp. 603-609, vol. 25.

Ngo et al., The protein folding problem and tertiary structure prediction, 1994, pp. 492-494.

Pellizzari et al., FEBS Letters, 1999, pp. 199-204, vol. 462.

Samaniego et al., Induction of Programmed Cell Death in Kaposi's Sarcoma Cells by Preparations of Human Chorionic Gonadotropin, Journal of the National Cancer Institute, Jan. 20, 1999, pp. 135-143, vol. 91, No. 2.

Smith et al., "Recent develpments in drug therapy for multiple sclerosis," Multiple Sclerosis, 1999, pp. 110-120, vol. 5.

Traystman, R., "Animal Models of Focal and Global Cerebral Ischemia," ILAR Journal, 2003, pp. 85-95, vol. 44, No. 2.

Weinberger et al., "Mechanisms Mediating Biologic Activity of Synthetic Proline, Glycine, and Hydroxyproline Polypeptides in Human Neurophils," Mediators of Inflammation, 2005, pp. 31-38, vol. 1.

Yang et al., "Increased cortical nuclear factor kappaB (NF-kappaB) DNA binding activity after traumatic brain injury in rats," Neuroscience Letters, 1995, pp. 101-104, vol. 197.

Abeyama et al., A role of NF-kappaB-dependent gene transactivation in sunburn. The Journal of Clinical Investigation, vol. 105, No. 12, pp. 1751-1759, Jun. 2000.

Cook et al., Modified total lymphoid irradiation and low does coricosteroids in progressive multiple sclerosis. Journal of Neurological Sciences, vol. 152, pp. 172-181, 1997.

Flores et al., NFkappaB and AP-1 DNA binding activity in patients with multiple sclerosis. J. Neuroimmunol. vol. 135, No. 1-2, pp. 141-147, Feb. 2003.

Oka et al., Immunosuppression in organ transplation, Japanese Journal of Pharmacology, vol. 71, No. 2, pp. 89-100, Jun. 1996.

Zhou et al., Transplantation tolerance in NF-kappaB-impaired mice is not due to regulation but is prevented transgenic expresion of Bcl-xL. The Journal of Immunology, vol. 174, No. 6, pp. 3447-3453, Mar. 2005.

* cited by examiner

IMMUNOREGULATORY COMPOSITIONS

CROSS-REFERENCE TO RELATED APPLICATION

This application is a continuation in part of U.S. Ser. No. 10/028,075, filed Dec. 21, 2001, a continuation of U.S. Ser. No. 10/262,522, filed Sep. 30, 2002, which is a continuation of International Application No. PCT/NL01/00259, designating the United States of America published in English as PCT International Publication No. WO 01/72831 A2 filed Mar. 3, 2001, and a continuation in part of International Application No. PCT/NL02/00639, designating the United States of America and published on Apr. 10, 2002 in English as PCT Internatinal Publication No. WO 03/029292 A2, the contents of all of each of which are incorporated by this reference.

TECHNICAL FIELD

The invention relates generally to biotechnology, and more specifically to compositions having immunoregulatory activity, which compounds include particular oligopeptides derived from human chorionic gonadotropin (hCG).

BACKGROUND

U.S. Pat. No. 5,380,668 to Herron (Jan. 10, 1995), the contents of the entirety of which are incorporated by this reference, discloses, among other things, various compounds having the antigenic binding activity of hCG. The oligopeptides disclosed therein are disclosed generally for use in diagnostice methods.

Various patents and patent applications to Gallo et al. (e.g., U.S. Pat. No. 5,677,275 (corresponding to WO 96/04008 A1), U.S. Pat. No. 5,877,148 (also corresponding to WO 96/04008 A1), WO 97/49721 A1, U.S. Pat. No. 6,319,504 (corresponding to WO 97/49373), U.S. Patent Application 2003/0049273 A1 (also corresponding to WO 97/49373), U.S. Pat. No. 5,968,513 (corresponding to WO 97/49418), U.S. Pat. No. 5,997,871 (corresponding to WO 97/49432), U.S. Pat. No. 6,620,416, U.S. Pat. No. 6,596, 688, WO 01/11048 A2, WO 01/10907 A2., and U.S. Pat. No. 6,583,109) relate to various oligopeptides and their use in, among other things, "inhibiting HIV infection", "treating or preventing HIV infection", "treating or preventing cancer", "treating or preventing a condition characterized by loss of body cell mass", "treating or preventing a condition associated with pathological angiogenesis", "treating or preventing hematopoietic deficiency", "ex vivo gene therapy", "expanding blood cells in vitro", and/or "providing blood cells to a subject".

DISCLOSURE OF THE INVENTION

As we described in PCT International Publication No. WO 03/029292 A2 (published Apr. 10, 2003), PCT International Publication No. WO 01/72831 A2 (published Oct. 4, 2001), and U.S. Patent Application Publications 20020064501 A1 (published May 30, 2002), 20030119720 A1 (published Jun. 26, 2003), 20030113733 A1 (published Jun. 19, 2003), and 20030166556 A1 (published Sep. 4, 2003), the contents of all of which are incorporated by this reference, compositions containing purified or isolated oligopeptides described herein have immunoregulatory activity useful in, for example, the treatment of sepsis and other disease states and conditions. They also have gene regulatory activities.

The invention thus includes a composition comprising a purified or isolated peptide consisting of particular four to eight amino acid segments of the sequence MTRVLQGV-LPALPQVVC (SEQ ID NO:44 of the incorporated herein SEQUENCE LISTING); and derivatives thereof having one or more conservative substitutions relative to the sequence of SEQ ID NO:44. The particular compositions exhibit immunoregulatory activity as determined by measuring the segment's ability to modulate production of NO by a cell. Preferably, the compositions have the ability to decrease shock in a subject (e.g., a mammal) undergoing sepsis.

In one embodiment, the amino acid segment includes a tetrameric sequence (corresponding to the LQVG (SEQ ID NO: 1) portion of SEQ ID NO:44, i.e.,

AAL AAQ AAG AAV wherein AAL is a substituted or unsubstituted non-polar amino acid selected from the group consisting of Ala and Leu; AAQ is a substituted or unsubstituted amino acid selected from the group consisting of Gln, Pro, and Ala; AAG is a substituted or unsubstituted Gly; and AAV is a substituted or unsubstituted non-polar amino acid selected from the group consisting of Val and Ala. For instance, the peptide could be selected from the group consisting of LQGV (SEQ ID NO:1), the derivative AQGV (SEQ ID NO:2), the derivative LQGA (SEQ ID NO:19), the derivative LAGV (SEQ ID NO:26), and the derivativeLPGC (SEQ ID NO:41).

In a different embodiment, the segment is the tetramer MTRV (SEQ ID NO:42) or QVVC (SEQ ID NO:43).

In another embodiment, the segment is six or seven amino acids long, and comprises the sequence AAV AAL Pro Arg AAL2 AAP wherein AAV is substituted or unsubstituted Val or Ala, wherein AAL and AAL2 are independently selected from substituted or unsubstituted Lys or Ala, and wherein AAP is a substituted or unsubstituted Pro or Ala.

In such an embodiment, the purified or isolated peptide can have a formula selected from the group consisting of VLPALP (SEQ ID NO:3), the derivative ALPALP (SEQ ID NO:21), the derivative VAPALP (SEQ ID NO:22), the derivative ALPALPQ (SEQ ID NO:23), the derivative VLPAAPQ (SEQ ID NO:24), the derivative VLPALAQ (SEQ ID NO:25), the derivative VLPALA (SEQ ID NO:28), VLPALPQ (SEQ ID NO:29), the derivative VLPALPA (SEQ ID NO:31), the derivative GVLPALP (SEQ ID NO:32), and the derivative VLAALP (SEQ ID NO:117).

In another embodiment, the composition has no more than eight amino acids, and includes an amino acid sequence consisting of:

AAL AAQ AAG AAV wherein AAL is a substituted or unsubstituted amino acid selected from the group of amino acids consisting of Ala, Leu, and Met, wherein AAQ is a substituted or unsubstituted amino acid selected from the group of amino acids consisting of Gln, Thr, Ala, and Pro, wherein AAG is substituted or unsubstituted Gly or Arg, and wherein AAV is a substituted or unsubstituted amino acid selected from the group of amino acids consisting of Cys, Ala, and Val. Again such a composition is characterized in having immunoregulatory activity as determined by: measuring its capability of modulating production of NO by a cell.

In such an embodiment, the sequence is preferably selected from the group consisting of Leu Gln Gly Val (SEQ ID NO:1), Ala Gln Gly Val (SEQ ID NO:2), Leu Gln Gly Ala (SEQ ID NO:19), Leu Ala Gly Val (SEQ ID NO:26), Leu Pro Gly Cys (SEQ ID NO:41), and Met Thr Arg Val (SEQ ID NO:42). Preferably, the composition is the sequence of SEQ ID NO:1, SEQ ID NO:2, SEQ ID NO:19, SEQ ID NO:26, SEQ ID NO:41, SEQ ID NO:42, or a salt of any thereof.

The invention further includes a pharmaceutical composition comprising a purified or isolated peptide, or acid addition salt thereof, the purified or isolated peptide (a) consisting of an amino acid sequence selected from the group consisting of: (i) a four to seven amino acid segment of the sequence of MTRVLQGVLPALPQVVC (SEQ ID NO:44); and (ii) a derivative of the segment of (a) having one or more conservative substitutions relative to the sequence of SEQ ID NO:44; and (b) exhibiting an immunoregulatory activity as determined by measuring its capability of modulating production of NO by a cell.

Such a pharmaceutical composition preferably includes a sequence selected from the group selected from the group consisting of LQGV (SEQ ID NO:1), AQGV (SEQ ID NO:2), VLPALP (SEQ ID NO:3), LQGA (SEQ ID NO:19), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLPALA (SEQ ID NO:28), VLPALPQ (SEQ ID NO:29), VLPALPA (SEQ ID NO:31), and GVLPALP (SEQ ID NO:32), LPGC (SEQ ID NO:41), MTRV (SEQ ID NO:42), QVVC (SEQ ID NO:43), VLAALP (SEQ ID NO:117), and combinations of any thereof, with or without other active or inactive ingredients, presented in a pharmaceutically acceptable form for administration to a human.

In one preferred embodiment, the inventin is a purified or isolated peptide consisting of GVLPALPQ (SEQ ID NO:33), or an acid addition salt thereof. The invention would thus also include a pharmaceutical composition comprising the peptide of SEQ ID NO:33 or an addition salt thereof, together with a pharmaceutically acceptable excipient.

In another embodiment the invention comprises a purified or isolated peptide (or, for example, acid addition salt thereof), selected from the group consisting of AQG, MTR, and VVC.

Finally the invention includes a composition comprising one or more of the following amino acid segments: LQGV (SEQ ID NO:1), AQGV (SEQ ID NO:2), VLPALP (SEQ ID NO:3), LQGA (SEQ ID NO:19), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLPALA (SEQ ID NO:28), VLPALPQ (SEQ ID NO:29), VLPALPA (SEQ ID NO:31), and GVLPALP (SEQ ID NO:32), LPGC (SEQ ID NO:41), MTRV (SEQ ID NO:42), QVVC (SEQ ID NO:43), VLAALP (SEQ ID NO:117), AQG, MTR, or VVC.

In another embodiment, the invention includes a composition comprising a purified or isolated peptide consisting of sequence LQG in an amount sufficient to exhibit an immunoregulatory activity as determined by measuring the sequence LQG's ability to modulate production of NO by a cell.

The invention provides a method for the treatment of bone disease such as osteoporosis comprising administering to a subject believed to be in need of such treatment a composition comprising an oligopeptide, derivative or functional analogue thereof, the particular molecule capable of modulating production of NO and/or TNF-alpha by a cell.

Such a method of treatment is particularly useful in post-menopausal women that no longer experience the benefits of being provided with a natural source of hCG and its breakdown products. Such a treatment can be achieved by systemic administration of a composition of the invention according to the invention, but local administration in joints, bursae or tendon sheaths is provided as well. The molecule can be selected from Table 6 or identified in a method described herein. The treatment comprises administering to the subject a pharmaceutical composition comprising an oligopeptide or functional analogue thereof capable of reducing production of NO by a cell, for example, wherein the composition comprises at least two oligopeptides or functional analogues thereof, each capable of reducing production of NO and/or TNF-alpha by a cell, in particular wherein the at least two oligopeptides are selected from the group LQGV (SEQ ID NO:1), AQGV (SEQ ID NO:2), and VLPALP (SEQ ID NO:3).

Several oligopeptides according to the invention have been tested, both ex vivo and in vivo, and in small animals. A beneficial effect of these oligopeptides on LPS-induced sepsis in mice, namely the inhibition of the effect of the sepsis, was observed. Immunomodulatory effects with these oligopeptides have been observed in vitro and in ex vivo such as in T-cell assays showing the inhibition of pathological Th1 immune responses, suppression of inflammatory cytokines (MIF), increase in production of anti-inflammatory cytokines (IL-10, TGF-beta) and immunomodulatory effects on antigen-presenting cells (APC) like dendritic cells, monocytes and macrophages.

Now knowing the gene modulatory effect of the composition of the inventions such as oligopeptides as provided herein allows for rational design of signal molecule mixtures that better alleviate the symptoms seen with sepsis. One such mixture, a 1:1:1 mixture of LQGV (SEQ ID NO:1), AQGV (SEQ ID NO:2) and VLPALP (SEQ ID NO:3) was administered to primates in a gram-negative induced rhesus monkey sepsis model for prevention of septic shock and found to be effective in this primate model. Accordingly, the invention provides a pharmaceutical composition for the treatment of sepsis in a primate and a method for the treatment of sepsis in a primate comprising subjecting the primate to a composition of the invention according to the invention, preferably to a mixture of such composition of the inventions. Administration of such a composition of the invention or mixture preferably occurs systematically, for example, by intravenous or intraperitoneal administration. In a further embodiment, such treatment also comprises the use of for example an antibiotic, however, only when such use is not contra indicated because of the risk of generating further toxin loads because of lysis of the bacteria subject to the action of those antibiotics in an individual thus treated.

The invention also provides use of a composition according to the invention for the preparation of a pharmaceutical composition or medicament and methods of treating various medical conditions that are other than use in the preparation of a pharmaceutical composition for the treatment of an immune-mediated disorder or a method of treatment of an immune-mediated disorder or treatment of a wasting syndrome.

DETAILED DESCRIPTION OF THE INVENTION

As used herein, a "purified or isolated" peptide is one that has been purified from a natural or biotechnological source, or, more preferably, is synthesized as described herein.

"Composition", as used herein, refers to chemical compounds which contain or consist of the oligopeptide. The oligopeptide is preferably isolated before inclusion within the composition. The oligopeptide most preferably consists of three (3) to six (6) amino acids.

For instance, the previously described preferred compound could, in one embodiment be:

NT AA1 AA2 AA3 AA4 CT wherein NT at the N-terminus is selected from the group of H—, CH3—, an acyl group, or a general protective group; and CT at the C-terminus is selected from the group of small (e.g. 1 to 5 amino acids) peptides, —OH, —OR$^1$, —NH$_2$, —NHR$^1$, —NR$^1$ R$^2$, or —N(CH$_2$)$_{1-6}$ NR$^1$ R$^2$, wherein R$^1$ and R$^2$, when present, are independently selected from H, alkyl, aryl, (ar)alkyl, and wherein R$^1$ and R$^2$ can be cyclically bonded to one another.

"Alkyl" as used herein, is preferably a saturated branched or unbranched hydrocarbon having one to six carbon atoms, e.g. methyl, ethyl, and isopentyl.

"Aryl" as used herein, is an aromatic hydrocarbon group, preferably having 6 to 10 carbon atoms, such as phenyl or naphthyl.

"(Ar)alkyl", as used herein, is an arene group (having both aliphatic and aromatic portions), preferably having 7 to 13 carbon atoms such as benzyl, ethylbenzyl, n-propylbenzyl, and isobutylbenzyl.

"Oligopeptide", as used herein are peptides having from 3 to 8 amino acids joined together by peptide bonds. Equivalent to oligopeptides are compounds having the same or equivalent sidechains as the particular amino acids used in an oligopeptide, and arranged sequentially in the same order as the peptides, but joined together by non-peptide bonds, e.g., by isosteric linkages such as the keto isostere, hydroxy isostere, diketo isostere, or the keto-difluoromethylene isostere.

"Composition" also includes, for example, an acceptable salt of the oligopeptide or a labeled oligopeptide. As used herein, "acceptable salt" refers to salts that retain the desired activity of the oligopeptide or equivalent compound, but preferably do not detrimentally affect the activity of the oligopeptide or other component of a system in which uses the oligopeptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt).

The thus developed chemical entity can be administered and introduced in-vivo systemically, topically, or locally. The peptide, or is modification or derivative, can be administered as the entity as such or as a pharmaceutically acceptable acid- or baseaddition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxahc acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

A "substitution" with regard to the various amino acids generally relate to substituting a group such as alkoxy, halogen, hydroxy, nitro, or lower alkyl onto an aromatic ring for a hydrogen that would usually be present. Substitutions can also be made on the alkyl chain connecting the aromatic portion to the peptide backbone, with, for instance lower alkyl groups substituting for a hydrogen. Still further substitutions can be made at the alpha position of an amino acid, also using an alkyl group.

Substitutions with regard to the amino acid phenylalanine include compounds such as L/D-homophenylalanyl, N methyl phenylalanyl, .alpha.-methylphenylalanyl, and alpha.-methyl-tyrosyl.

Preferred substitutions involve the use of fluorine or chlorine as a halogen, and methoxy as an alkoxy group. With regard to alkyl and lower alkyl, generally alkyl groups having fewer (1 to 3) carbon atoms are preferred.

The compounds according to the general formula may be prepared in a manner conventional for such compounds. To that end, suitably N alpha. protected (and side-chain protected if reactive side-chains are present) amino acid derivatives or peptides are activated and coupled to suitably carboxyl protected amino acid or peptide derivatives either in solution or on a solid support. Protection of the .alpha.-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The Z group can also be removed by catalytic hydrogenation, Other suitable protecting groups include the Nps, Bmv, Bpoc, Aloc, MSC, etc. A good overview of amino protecting groups is given in *The peptides, Analysis, Synthesis, Biology*, Vol. 3 E. Gross and J. Meienhofer, eds., (Academic Press, New York, 1981). Protection of carboxyl groups can take place by ester formation, for example, base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology, id.* or in *Pure and Applied Chemistry*, 59(3), 331-344 (1987). Activation of the carboxyl group of the suitably protected amino acids or peptides can take place by the azide, mixed anhydride, active ester, or carbodiimide method especially with the addition of catalytic and racemization-suppressing compounds like 1-N—N-hydroxybenzotriazole, N-hydroxysuccin-imide, 3-hydroxy-4-oxo-3,4-dihydro-1,2,3,-benzotriazine, N-hydroxy-5 norbornene-2,3-dicarboxyimide. Also the anhydrides of phosphorus based acids can be used. See, e.g., *The Peptides, Analysis, Synthesis, Biology*, supra and *Pure and Applied Chemistry*, 59(3), 331-344 (1987).

It is also possible to prepare the compounds by the solid phase method of Merrifield. Different solid supports and different strategies are known see, e.g. Barany and Merrifield in *The Peptides, Analysis, Synthesis, Biology*, Vol. 2, E. Gross and J. Meienhofer, eds., (Acad. Press, New York, 1980), Kneib-Cordonier and Mullen *Int. J. Peptide Protein Res.*, 30, 705-739 (1987) and Fields and Noble *Int. J. Peptide Protein Res.*, 35, 161-214 (1990). The synthesis of compounds in which a peptide bond is replaced by an isostere, can, in general, be performed using the previously described protecting groups and activation procedures. Procedures to synthesize the modified isosteres are described in the literature e.g. for the—CH$_2$—NH—isostere and for the—CO—CH$_2$—isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g. volumes 3, 5 and 9 of the series on *The Peptides Analysis, Synthesis, Biology*, supra.

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds., (Acad. Press, New York, 1987).

Although possibly not desirable from an economic point of view, oligopeptides according to the invention could also be made according to recombinant DNA methods. Such methods involve the preparation of the desired oligopeptide thereof by means of expressing recombinant polynucleotide sequence which codes for one or more of the oligopeptides in question in a suitable microorganism as host. Generally the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eucaryotic or procaryotic host cell, and culturing the host cell thus transformed. When a eucaryotic host cell is used, the compound may include a glycoprotein portion.

As used herein, a "functional analogue" or "derivative" of a peptide includes an amino acid sequence, or other sequence monomers, which has been altered such that the functional properties of the sequence are essentially the same in kind, not necessarily in amount. An analogue or derivative can be provided in many ways, for instance, through "conservative amino acid substitution". Also peptidomimetic compounds can be designed that functionally or structurally resemble the original peptide taken as the starting point but that are for example composed of non-naturally occurring amino acids or polyamides. With "conservative amino acid substitution", one amino acid residue is substituted with another residue with generally similar properties (size, hydrophobicity), such that the overall functioning is likely not to be seriously affected. However, it is often much more desirable to improve a specific function. A derivative can also be provided by systematically improving at least one desired property of an amino acid sequence. This can, for instance, be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

A derivative or analogue can also be, for instance, generated by substitution of an L-amino acid residue with a D-amino acid residue. This substitution, leading to a peptide which does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics.

A person skilled in the art is well able to generate analogous compounds of an amino acid sequence. This can, for instance, be done through screening of a peptide library. Such an analogue has essentially the same functional properties of the sequence in kind, not necessarily in amount. Also, peptides or analogues can be circularized, for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation.

Synthetic versions of these oligopeptides as described above, and functional analogues or derivatives of these breakdown products, are herein provided to modulate gene expression in a cell and be used in methods to rectify errors in gene expression or the treatment of disease.

The term "pharmaceutical composition" as used herein is intended to cover both the active composition of the invention alone or a composition containing the composition of the invention together with a pharmaceutically acceptable carrier, diluent or excipient. Acceptable diluents of an oligopeptide as described herein in the detailed description are for example physiological salt solutions or phosphate buffered salt solutions. In one embodiment, a signal molecule is administered in an effective concentration to an animal or human systemically, e.g., by intravenous, intramuscular or intraperitoneal administration. Another way of administration comprises perfusion of organs or tissue, be it in vivo or ex vivo, with a perfusion fluid comprising a signal molecule according to the invention. Topical administration, e.g., in ointments or sprays, may also apply, e.g., in inflammations of the skin or mucosal surfaces of for example mouth, nose and/or genitals. Local administration can occur in joints, bursae, tendon sheaths, in or around the spinal cord at locations where nerve bundles branch off, at the location of hernias, in or around infarcted areas in brain or heart, etc. The administration may be done as a single dose, as a discontinuous sequence of various doses, or continuously for a period of time sufficient to permit substantial modulation of gene expression. In the case of a continuous administration, the duration of the administration may vary depending upon a number of factors which would readily be appreciated by those skilled in the art.

The administration dose of the active molecule may be varied over a fairly broad range. The concentrations of an active molecule which can be administered would be limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

The active molecule may be administered directly in a suitable vehicle, such as, for example, phosphate-buffered saline (PBS) or solutions in alcohol or DMSO. Pursuant to preferred embodiments of the present invention, however, the active molecule is administered through a single dose delivery using a drug-delivery system, such as a sustained-release delivery system, which enables the maintenance of the required concentrations of the active molecule for a period of time sufficient for adequate modulation of gene expression. A suitable drug-delivery system would be pharmacologically inactive or at least tolerable. It should preferably not be immunogenic nor cause inflammatory reactions, and should permit release of the active molecule so as to maintain effective levels thereof over the desired time period. Alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers and implants; and polymeric delivery materials, such as polyethylene oxide/polypropylene oxide block copolymers, polyesters, cross-linked polyvinylalcohols, polyanhydrides, polymethacrylate and polymethacrylamide hydrogels, anionic carbohydrate polymers, etc. Useful delivery systems are well known in the art.

A highly suitable formulation to achieve the active molecule release comprises injectable microcapsules or microspheres made from a biodegradable polymer, such as poly (dl-lactide), poly(dl-lactide-co-glycolide), polycaprolactone, polyglycolide, polylactic acid-co-glycolide, poly(hydroxybutyric acid), polyesters or polyacetals. Injectable systems comprising microcapsules or microspheres having a diameter of about 50 to about 500 micrometers offer advantages over other delivery systems. For example, they generally use less active molecules and may be administered by paramedical personnel. Moreover, such systems are inherently flexible in the design of the duration and rate of separate drug release by selection of microcapsule or microsphere size, drug loading and dosage administered. Further, they can be successfully sterilized by gamma irradiation.

The design, preparation, and use of microcapsules and microspheres are well within the reach of persons skilled in the art and detailed information concerning these points is available in the literature. Biodegradable polymers (such as lactide, glycolide and caprolactone polymers) may also be used in formulations other than microcapsules and microspheres; e.g., premade films and spray-on films of these polymers containing the active molecule would be suitable for use in accordance with the present invention. Fibers or filaments comprising the active molecule are also contemplated as within the scope of the present invention.

Another highly suitable formulation for a single-dose delivery of the active molecule in accordance with the present invention involves liposomes. The encapsulation of an active molecule in liposomes or multilamellar vesicles is a well-known technique for targeted drug delivery and prolonged drug residence. The preparation and use of drug-loaded liposomes is well within the reach of persons skilled in the art and well documented in the literature.

Yet another suitable approach for single-dose delivery of an active molecule in accordance with the present invention involves the use of viscous installates. In this technique, high molecular weight carriers are used in admixture with the active molecule, giving rise to a structure which produces a solution with high viscosity. Suitable high molecular weight carriers include, but are not limited to, the following: dextrans and cyclodextrans; hydrogels; (cross-linked) viscous materials, including (cross-linked) viscoelastics; carboxymethylcellulose; hyaluronic acid; and chondroitin sulfate. The preparation and use of drug-loaded viscous instillates is well known to persons skilled in the art.

Pursuant to yet another approach, the active molecule may be administered in combination with absorbable mechanical barriers such as oxidized regenerated cellulose. The active molecule may be covalently or non-covalently (e.g., ionically) bound to such a barrier, or it may simply be dispersed therein.

The invention is further explained with the aid of the following illustrative examples.

EXAMPLES

Example I

Material and Methods

PEPTIDE SYNTHESIS: The peptides as mentioned herein such as LQG, AQG, LQGV (SEQ ID NO:1), AQGV (SEQ ID NO:2), LQGA (SEQ ID NO:19), VLPALP (SEQ ID NO:13), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLAALP (SEQ ID NO:27), VLPALA (SEQ ID NO:28), VLPALPQ (SEQ ID NO:29), VLAALPQ (SEQ ID NO:30), VLPALPA (SEQ ID NO:31), GVLPALP (SEQ ID NO:32), VVCNYRDVRFESIRLPGCPRGVNPV-VSYAVALSCQCAL (SEQ ID NO:35), RPRCRPINAT-LAVEKEGCPVCITVNTTICAGYCPT (SEQ ID NO:45), SKAPPPSLPSPSRLPGPS (SEQ ID NO:38), LQGVL-PALPQVVC (SEQ ID NO:34), SIRLPGCPRGVNPVVS (SEQ ID NO:39), LPGCPRGVNPVVS (SEQ ID NO:40), LPGC (SEQ ID NO:41), MTRV (SEQ ID NO:42), MTR, and VVC were prepared by solid-phase synthesis (R. B. Merrifield, *J. Am. Chem. Soc.*, 85:2149-2165 (1963)) using the fluorenylmethoxycarbonyl (Fmoc)/tert-butyl-based methodology (Atherton, 1985) with 2-chlorotrityl chloride resin (Barlos et al., *Int. J. Peptide Protein res.*, 37:513-520 (1991)) as the solid support.

The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H$_2$O/triisopropylsilane (TIS) 95:2.5:2.5. After 30 minutes, TIS was added until decolorization. The solution was evaporated in vacuo and the peptide precipitated with diethylether.

The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example, for peptides LQG and LQGV (SEQ ID NO:1): 10 minutes 100% A followed by linear gradient 0-10% B in 50 minutes. For example for peptides VLPALP (SEQ ID NO:3) and VLPALPQ (SEQ ID NO:29): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The eluate was concentrated and lyphilized in 28 hours. Peptides later were prepared for use by dissolving them in PBS.

Example II

Endotxin Shock Model (Sepsis)

Sepsis. For the endotoxin model, BALB/c mice were injected i.p. with 8-9 mg/kg LPS (*E. coli* 026:B6; Difco Lab., Detroit, Mich., USA). Control groups (PBS) were treated with PBS i.p. only. To test the effect of NMPF from different sources (synthetic, commercial hCG preparation [c-hCG]), we treated BALB/c mice with a dose of 300-700 IU of different hCG preparations (PG23; PREGNYL™ batch no. 235863, PG25; PREGNYL™ batch no. 255957 from NV Organon of Oss, NL) and with synthetic peptides (5 mg/kg) after two hours of LPS injection. In other experiments, BALB/c mice were injected i.p. either with 10 mg/kg or with 11 mg/kg LPS (*E. coli* 026:B6; Difco Lab., Detroit, Mich., USA). Subsequently, mice were treated after 2 hours and 24 hours of LPS treatment with NMPF peptides.

Semi-quantitative sickness measurements. Mice were scored for sickness severity using the following measurement scheme:
1 Percolated fur, but no detectable behaviour differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund)
6 Sacrificed Results Endotoxin Shock Model (Sepsis)

Sepsis experiments. To determine the effect of synthetic peptides (NMPF) in high-dose LPS shock model, BALB/c mice were injected intraperitoneally with different doses of LPS and survival was assessed daily for 5 days. In this experiment (for the LPS endotoxin model), BALB/c mice were injected i.p. with 8-9 mg/kg LPS (*E. coli* 026:B6; Difco Lab., Detroit, MI, USA). Control groups (PBS) were treated with PBS i.p. only. We treated BALB/c mice with a dose of 300-700 IU of different hCG preparations (PG23; PREGNYL batch no. 235863, PG25; PREGNYL batch no. 255957) or with peptides (5 mg/kg) after two hours of LPS injection.

These experiments showed (Table 1) that NMPF peptides 4, 6, 66 and PG23 inhibited shock completely (all mice had in first 24 hours sickness scores not higher than 2; shortly thereafter they recovered completely and had sickness scores of 0), while peptides 2, 3 and 7 accelerated shock (all mice had in first 24 hours sickness scores of 5 and most of them died, while the control mice treated with LPS+PBS had sickness scores of 3-4 in first 24 hours and most of them died after 48 hours with sickness scores of 5; 17% survival rate at 72 hours). In addition, peptides 1, 5, 8, 9, 11, 12, 13, 14 and 64 showed in a number of different experiments variability in effectiveness as well as in the kind (inhibitory vs accelerating) of activity. This variability is likely attributable to the rate of breakdown of the various peptides and the different effects the various peptides and their breakdown products have in vivo. In addition, these experiments also showed the variability in anti-shock activity in c-hCG preparations that is likely attributable to the variation in the presence of anti-shock and shock-accelerating NMPF. Visible signs of sickness were apparent in all of the experimental animals, but the kinetics and obviously the severity of this sickness were significantly different. These data are representative of at least 10 separate experiments.

In Table 2, we see the effect of ALA-replacement (PEPSCAN) in peptide LQG, LQGV (SEQ ID NO:1), VLPALP (SEQ ID NO:3), VLPALPQ (SEQ ID NO:29) in septic shock experiments. We conclude that the change in even one amino acid by a neutral amino acid can lead to different activity. So, genomic differences as well as polymorphism in these peptides can regulate the immune response very precisely. Derivatives of these peptides, for example (but not limited to) by addition of classical and non-classical amino acids or derivatives that are differentially modified during or after synthesis, for example benzylation, amidation, glycosylation, proteolytic cleavage, linkage to an antibody molecule or other cellular ligand, etc. could also lead to a better effectiveness of the activity.

To determine whether treatment of BALB/c mice with NMPF inhibits septic shock at different stages of disease, synthetic peptides (NMPF) were injected i.p. at 2 and 24 hours after the induction of septic shock with high dose LPS (10 mg/kg).

As shown in Tables 3 and 4, control mice treated with PBS after the shock induction reached a sickness score of 5 at 14 and 24 hours, and remained so after the second injection with PBS. The survival rate in control group mice was 0% at 48 hours. In contrast to control mice, mice treated with NMPF 9, 11, 12, 43, 46, 50 and 60 reached a maximum sickness score of 2-3 at 24 hours after the induction of septic shock and further reached a maximum sickness score of 1-2 at 48 hours after the second injection of NMPF. In addition, mice treated with NMPF 5, 7, 8, 45, 53 and 58 reached a sickness score of 5 and after the second injection with NMPF all mice returned to a sickness score of 1-2 and survival rates in NMPF groups were 100%. Mice treated with NMPF 3 reached sickness scores of 3-4 and the second NMPF injection did save these mice. These experiments show that NMPF peptides have anti-shock activity at different stages of the disease and NMPF have anti-shock activity even at the disease stage when otherwise irreversible damage had been done. This indicates that NMPF have effects on different cellular levels and also have repairing and regenerating capacity.

Example III

NOD Experiment

Mice. Female NOD mice at the age of 13-14 weeks were treated i.p. with PBS (n=6) or NMPF peptides (VLPALPQVVC (SEQ ID NO:20), LQGV (SEQ ID NO:1), GVLPALPQ (SEQ ID NO:33), VLPALP (SEQ ID NO:3), VLPALPQ (SEQ ID NO:29), MTRV (SEQ ID NO:42), LPGCPRGVNPVVS (SEQ ID NO:40), CPRGVNPVVS (SEQ ID NO:50), LPGC (SEQ ID NO:41), MTRVLQGVLPALPQVVC (SEQ ID NO:44), VVCNYRDVRFESIRLPGCPRGVNPVVSYAVALSCQCAL (SEQ ID NO:35)) (5 mg/kg, n=6) three times a week for 2 weeks. Every four days urine was checked for the presence of glucose (Gluketur Test; Boehringer Mannheim, Mannheim, Del.). All mice used in these studies were maintained in a pathogen-free facility. They were given free access to food and water. The experiments were approved by the Animal Experiments Committee of the Erasmus University Rotterdam. Diabetes was assessed by measurement of the venous blood glucose level using an Abbott Medisense Precision glucometer. Mice were considered diabetic after two consecutive glucose measurements $\geq 11$ mmol/l (200 mg/dl). Onset of diabetes was dated from the first consecutive reading.

Glucose tolerance test (GTT) was performed at 28 weeks of age in fasted mice (n=5) by injecting 1 g/kg D-glucose intraperitoneally (i.p.). At 0 (fasting), 5, 30 and 60 minutes, blood samples were collected from the tail and tested for glucose content.

Example IV

NO Experiment

Cell culture. The RAW 264.7 murine macrophage cell line, obtained from American Type Culture Collection (Manassas, Va., USA), were cultured at 37° C. in 5% $CO_2$ using DMEM containing 10% fetal calf serum (FCS), 50 U/ml penicillin, 50 µg/ml streptomycin, 0.2 M Na-pyruvate, 2 mM glutamine and 50 µM 2-mercaptoethanol (Bio Whittaker, Europe). The medium was changed every 2 days.

Nitrite measurements. Nitrite production was measured in the RAW 264.7 macrophage supernatants. The cells (7.5× $10^5$/ml) were cultured in 48-well plates in 500 µl of culture medium. The cells were stimulated with LPS (10 microg/ml) and/or NMPF (1 pg/ml, 1 ng/ml, 1 µg/ml) for 24 hours, then the culture media were collected. Nitrite was measured by adding 100 microl of Griess reagent (Sigma) to 100 microl samples of culture medium. The $OD_{540}$ was measured using a microplate reader, and the nitrite concentration was calculated by comparison with the $OD_{540}$ produced using standard solutions of sodium nitrite in the culture medium.

Results

NOD Experiment

In order to determine whether NMPF has effect on the disease development in NOD mice, we tested NMPF on pre-diabetic female NOD mice at the age of 13-14 weeks. After only two weeks of treatment (injection of NMPF (5 mg/kg) every other day), glucosuria data of all NOD mice was analyzed at the of 17 weeks. Profound anti-diabetic effect (mice negative for glucosuria) was observed in different NMPF groups as compared to the PBS group, especially in NMPF groups treated with peptide VLPALPQVVC (SEQ ID NO:20), VLPALP (SEQ ID NO:3), MTRV (SEQ ID NO:42), LPGCPRGVNPVVS (SEQ ID NO:40) and LPGC. In addition, impairment of the glucose tolerance test was positively correlated to insulitis, but negatively correlated to the number of functional beta cells; also this test showed that NOD mice successfully treated with NMPF were tolerant for glucose as compared to the PBS group. Our results show that PBS treated NOD mice were all diabetic at the age of 23 weeks. Whereas, NOD mice treated three times a week for two weeks with NMPF showed profound inhibition of diabetes development. The strongest anti-diabetic effects were seen with NMPF-1, -4, -5, -6, -7, -65, -66 and commercial hCG preparation (PREGNYL, batch no. 235863). These mice had a low fasting blood glucose level and were tolerant for glucose (data partially shown). However, NMPF-71 showed no effect on the incidence of diabetes, while NMPF-64 and NMPF-11 had a moderate anti-diabetic effect.

NO Experiment

NO production is a central mediator of the vascular and inflammatory response. Our results show that macrophages (RAW 264.7) stimulated with LPS produce large amounts of NO. However, these cells co-stimulated with most of the NMPF peptides (NMPF peptides 1 to 14, 43 to 66 and 69) even in a very low dose (1 pg/ml) inhibited the production of NO.

Results apoE Experiment

The invention provides a method and a composition of the invention for the treatment of conditions that are associated with dysfunctional LDL receptors such as apoE and other members of the apolipoprotein family. In particular, use of a composition of the invention comprising GVLPALPQ (SEQ ID NO:33) (NMPF-5) and/or VLPALP (SEQ ID NO:3) (NMPF-6) or a functional analogue or derivative thereof is preferred. Groups of apoE deficient mice (n=6 per group) were fed a high cholesterol food and given PBS or NMPF every other day intraperitoneally. After 2.5 weeks, body weight was determined as shown in the Table below.

|  | Average Weight (g) | SD (g) | p-value |
|---|---|---|---|
| ApoE-/-PBS | 31.667 | 1.007 |  |
| ApoE-/-NMPF-4 | 31.256 | 1.496 | 0.536 |
| ApoE-/-NMPF-5 | 29.743 | 1.160 | 0.019 |
| Background/PBS | 26.760 | 1.582 | $10^{-6}$ |
| ApoE-/-NMPF-6 | 29.614 | 1.064 | 0.004 |

TABLE 1

Results of shock experiments in mice

| TEST SUBSTANCE | | % SURVIVAL IN TIME (HRS) | | | |
|---|---|---|---|---|---|
| | | 0 | 16 | 40 | 72 |
| PBS | | 100 | 100 | 67 | 17 |
| PG23 | | 100 | 100 | 100 | 100 |
| PG25 | | 100 | 83 | 83 | 83 |
| PEPTIDE NMPF | SEQUENCE | | | | |
| 1 | VLPALPQVVC (SEQ ID NO:20) | 100 | 100 | 50 | 17 |
| 2 | LQGVLPALPQ (SEQ ID NO:49) | 100 | 67 | 0 | 0 |
| 3 | LQG | 100 | 83 | 20 | 17 |
| 4 | LQGV (SEQ ID NO:1) | 100 | 100 | 100 | 100 |
| 5 | GVLPALPQ (SEQ ID NO:33) | 100 | 100 | 80 | 17 |
| 6 | VLPALP (SEQ ID NO:3) | 100 | 100 | 100 | 100 |
| 7 | VLPALPQ (SEQ ID NO:168) | 100 | 83 | 0 | 0 |
| 8 | GVLPALP (SEQ ID NO:32) | 100 | 100 | 83 | 67 |
| 9 | VVC | 100 | 100 | 50 | 50 |
| 11 | MTRV (SEQ ID NO:42) | 100 | 100 | 67 | 50 |
| 12 | MTR | 100 | 100 | 67 | 50 |

TABLE 1-continued

Results of shock experiments in mice

| | | % SURVIVAL IN TIME (HRS) | | | |
|---|---|---|---|---|---|
| | | 0 | 16 | 40 | 72 |
| 13 | LQGVLPALPQVVC (SEQ ID NO:34) | 100 | 100 | 100 | 100 |
| 14 | (CYCLIC) LQGVLPALPQVVC (SEQ ID NO:34) | 100 | 83 | 83 | 83 |
| 64 | LPGCPRGVNPVVS (SEQ ID NO:40) | 100 | 100 | 100 | 100 |
| 66 | LPGC (SEQ ID NO:41) | 100 | 100 | 100 | 100 |

TABLE 2

Additional results of shock experiments

| NMPF SEQUENCE ID: | ANTI-SHOCK EFFECT |
|---|---|
| LQGV (SEQ ID NO:1) | +++ |
| AQGV (SEQ ID NO:2) | +++ |
| LQGA (SEQ ID NO:19) | +++ |
| VLPALP (SEQ ID NO:3) | +++ |
| ALPALP (SEQ ID NO:21) | ++ |
| VAPALP (SEQ ID NO:22) | ++ |
| ALPALPQ (SEQ ID NO:23) | ++ |
| VLPAAPQ (SEQ ID NO:24) | ++ |
| VLPALAQ (SEQ ID NO:25) | +++ |
| | SHOCK ACCELERATING EFFECT |
| LAGV (SEQ ID NO:26) | +++ |
| LQAV (SEQ ID NO:52) | +++ |
| VLAALP (SEQ ID NO:27) | +++ |

TABLE 2-continued

Additional results of shock experiments

| NMPF SEQUENCE ID: | |
|---|---|
| VLPAAP (SEQ ID NO:117) | +++ |
| VLPALA (SEQ ID NO:28) | +++ |
| VLPALPQ (SEQ ID NO:29) | +++ |
| VLAALPQ (SEQ ID NO:30) | +++ |
| VLPALPA (SEQ ID NO:31) | +++ |

TABLE 3

Further additional results of shock experiments

| | % SURVIVAL IN TIME (HRS) | | | |
|---|---|---|---|---|
| NMPF PEPTIDES | Tx 0 | 14 | Tx 24 | 48 |
| PBS | 100 | 100 | 100 | 0 |
| NMPF-3 | 100 | 100 | 100 | 0 |
| NMPF-5 | 100 | 100 | 100 | 100 |
| NMPF-7 | 100 | 100 | 100 | 67 |
| NMPF-8 | 100 | 100 | 100 | 100 |
| NMPF-9 | 100 | 100 | 100 | 100 |
| NMPF-11 | 100 | 100 | 100 | 100 |
| NMPF-12 | 100 | 100 | 100 | 100 |
| NMPF-43 | 100 | 100 | 100 | 100 |
| NMPF-45 | 100 | 100 | 100 | 100 |
| NMPF-46 | 100 | 100 | 100 | 100 |
| NMPF-50 | 100 | 100 | 100 | 100 |
| NMPF-53 | 100 | 100 | 100 | 100 |
| NMPF-58 | 100 | 100 | 100 | 100 |
| NMPF-60 | 100 | 100 | 100 | 100 |

TABLE 4

Further additional results

| | SICKNESS SCORES | | | |
|---|---|---|---|---|
| NMPF PEPTIDES | Tx 0 | 14 | Tx 24 | 48 |
| PBS | 0, 0, 0, 0, 0 | 5, 5, 5, 5, 4, 4 | 5, 5, 5, 5, 5, 5 | ††††††† |
| NMPF-3 | 0, 0, 0, 0, 0 | 3, 3, 3, 3, 3, 4 | 4, 4, 4, 4, 4, 4 | †††††† |
| NMPF-5 | 0, 0, 0, 0, 0 | 5, 5, 5, 5, 5, 5 | 5, 5, 5, 5, 5, 5 | 2, 2, 2, 2, 2, 2 |
| NMPF-7 | 0, 0, 0, 0, 0 | 1, 1, 4, 4, 4, 4 | 5, 5, 5, 5, 5, 5 | 2, 2, 2, 2, †† |
| NMPF-8 | 0, 0, 0, 0, 0 | 3, 3, 5, 5, 5, 5 | 5, 5, 5, 5, 5, 5 | 2, 2, 4, 4, 4, 5 |
| NMPF-9 | 0, 0, 0, 0, 0 | 3, 3, 4, 4, 5, 5 | 2, 2, 2, 2, 2, 2 | 1, 1, 2, 2, 2, 2 |
| NMPF-11 | 0, 0, 0, 0, 0 | 1, 1, 3, 3, 4, 4 | 2, 2, 2, 2, 4, 4 | 1, 1, 1, 1, 1, 1 |
| NMPF-12 | 0, 0, 0, 0, 0 | 1, 1, 1, 1, 3, 3 | 1, 1, 1, 1, 1, 1 | 1, 1, 1, 1, 1, 1 |
| NMPF-43 | 0, 0, 0, 0, 0 | 1, 1, 4, 4, 4, 4 | 1, 1, 1, 1, 3, 3 | 2, 2, 2, 2, 2, 2 |

TABLE 4-continued

Further additional results

SICKNESS SCORES

| NMPF PEPTIDES | Tx 0 | 14 | Tx 24 | 48 |
|---|---|---|---|---|
| NMPF-45 | 0, 0, 0, 0, 0, 0 | 5, 5, 5, 5, 4, 4 | 3, 3, 4, 4, 5, 5 | 2, 2, 4, 4, 5, 5 |
| NMPF-46 | 0, 0, 0, 0, 0, 0 | 1, 1, 2, 2, 3, 3 | 1, 1, 2, 2, 2, 2 | 1, 1, 1, 1, 1, 1 |
| NMPF-50 | 0, 0, 0, 0, 0, 0 | 1, 1, 1, 1, 3, 3 | 2, 2, 2, 2, 3, 3 | 1, 1, 1, 1, 1, 1 |
| NMPF-53 | 0, 0, 0, 0, 0, 0 | 5, 5, 5, 5, 5, 5 | 5, 5, 5, 5, 5, 5 | 1, 1, 2, 2, 2, 2 |
| NMPF-58 | 0, 0, 0, 0, 0, 0 | 5, 5, 5, 5, 3, 3 | 5, 5, 5, 5, 3, 3 | 1, 1, 1, 1, 1, 1 |
| NMPF-60 | 0, 0, 0, 0, 0, 0 | 1, 1, 4, 4, 2, 2 | 2, 2, 2, 2, 4, 4 | 1, 1, 1, 1, 1, 1 |

TABLE 5

Summary of results of the various peptides in the various experiments.

| ID | SEQUENCE | SEPSIS | ANGIOGENSIS | CAO | DC | NOD |
|---|---|---|---|---|---|---|
| NMPF-1 | VLPALPQVVC (SEQ ID NO:20) | -+ |  |  | + | + |
| NMPF-2 | LQGVLPALPQ (SEQ ID NO:49) | -+ |  |  | + |  |
| NMPF-3 | LQG | -+ | + | + | + |  |
| NMPF-4 | LQGV (SEQ ID NO:1) | + | + | + | + |  |
| NMPF-5 | GVLPALPQ (SEQ ID NO:33) | -+ |  |  | + |  |
| NMPF-6 | VLPALP (SEQ ID NO:3) | + | + | + | + |  |
| NMPF-7 | VLPALPQ (SEQ ID NO:29) | + | + |  | + |  |
| NMPF-8 | GVLPALP (SEQ ID NO:32) | -+ |  |  | + |  |
| NMPF-9 | VVC | + | + |  | + |  |
| NMPF-10 | QVVC (SEQ ID NO:43) |  |  |  |  |  |
| NMPF-11 | MTRV (SEQ ID NO:42) | + | + |  | + | + |
| NMPF-12 | MTR | -+ | + |  | + |  |
| NMPF-13 | LQGVLPALPQVVC (SEQ ID NO:34) | + |  |  | + |  |
| NMPF-14 | cyclic-LQGVLPALPQVVC (SEQ ID NO:34) | + |  |  |  |  |
| NMPF-43 | AQG | + | + |  | + |  |
| NMPF-44 | LAG |  | + |  |  |  |
| NMPF-45 | LQA | + | + |  |  |  |
| NMPF-46 | AQGV (SEQ ID NO:2) | + | + |  | + |  |
| NMPF-47 | LAGV (SEQ ID NO:26) | -+ |  |  | + | + |
| NMPF-48 | LQAV (SEQ ID NO:52) |  |  |  |  |  |
| NMPF-49 | LQGA (SEQ ID NO:19) | + |  |  |  |  |
| NMPF-50 | ALPALP (SEQ ID NO:21) | + |  |  | + |  |
| NMPF-51 | VAPALP (SEQ ID NO:22) | + | + |  |  |  |
| NMPF-52 | VLAALP (SEQ ID NO:27) |  |  |  |  |  |
| NMPF-53 | VLPAAP (SEQ ID NO:117) | + |  |  | + |  |
| NMPF-54 | VLPALA (SEQ ID NO:28) |  |  |  |  |  |
| NMPF-55 | ALPALPQ (SEQ ID NO:23) | + |  |  |  |  |
| NMPF-56 | VAPALPQ (SEQ ID NO:173) |  | + |  |  |  |

TABLE 5-continued

Summary of results of the various peptides in the various experiments.

| ID | SEQUENCE | SEPSIS | ANGIOGENSIS | CAO | DC | NOD |
|---|---|---|---|---|---|---|
| NMPF-57 | VLAALPQ (SEQ ID NO:30) | | | | | |
| NMPF-58 | VLPAAPQ (SEQ ID NO:24) | + | | | + | |
| NMPF-59 | VLPALAQ (SEQ ID NO:25) | + | + | | | |
| NMPF-60 | VLPALPA (SEQ ID NO:31) | + | | | + | |
| NMPF-61 | VVCNYRDVRFESIRLPGCPRGVNPVVSYAVALSCQCAL (SEQ ID NO:35) | -+ | | | + | |
| NMPF-62 | VVCNYRDVRFESIRLPGCPRGVNPVVSYAVALSCQ (SEQ ID NO:169) | | | | | |
| NMPF-63 | SIRLPGCPRGVNPVVS (SEQ ID NO:39) | -+ | | | | |
| NMPF-64 | LPGCPRGVNPVVS (SEQ ID NO:40) | | | | + | |
| NMPF-65 | CPRGVNPVVS (SEQ ID NO:50) | | | | | |
| NMPF-66 | LPGC (SEQ ID NO:41) | + | + | | + | |
| NMPF-67 | CPRGVNP (SEQ ID NO:170) | | | | | |
| NMPF-68 | PGCP (SEQ ID NO:10) | -+ | | | | |
| NMPF-69 | RPRCRPINATLAVEKEGCPVCITVNTTICAGYCPT (SEQ ID NO:45) | | | | | |
| NMPF-70 | MTRVLQGVLPALPQ (SEQ ID NO:171) | -+ | | | | |
| NMPF-71 | MTRVLPGVLPALPQVVC (SEQ ID NO:174) | -+ | | | | |
| NMPF-74 | CALCRRSTTDCGGPKDHPLTC (SEQ ID NO:46) | | | | | |
| NMPF-75 | SKAPPPSLPSPSRLPGPC (SEQ ID NO:172) | | | | | |
| NMPF-76 | TCDDPRFQDSSSSKAPPPSLPSPSRLPGPSDTPILPQ (SEQ ID NO:48) | | | | | |

+ = effects;
-+ = variable effect;
no entry is no effect or not yet tested when table was assembled

TABLE 6

MODULATION OF NO AND/OR TNF-α

| ID | SEQUENCE | TNF-A | NO | TNF-A and NO |
|---|---|---|---|---|
| NMPF-1 | VLPALPQVVC (SEQ ID NO:20) | ++ | ++++ | ++++ |
| NMPF-2 | LQGVLPALPQ (SEQ ID NO:49) | -+ | ++++ | ++++ |
| NMPF-3 | LQG | + | ++++ | ++++ |
| NMPF-4 | LQGV (SEQ ID NO:1) | ++++ | ++++ | +++++++ |
| NMPF-5 | GVLPALPQ (SEQ ID NO:33) | ++++ | ++++ | +++++++ |
| NMPF-6 | VLPALP (SEQ ID NO:3) | ++++ | ++++ | +++++++ |
| NMPF-7 | VLPALPQ (SEQ ID NO:29) | ++++ | ++++ | +++++++ |
| NMPF-8 | GVLPALP (SEQ ID NO:32) | ++++ | ++++ | +++++++ |
| NMPF-9 | VVC | ++++ | ++++ | +++++++ |
| NMPF-10 | QVVC (SEQ ID NO:43) | ++++ | +++ | ++++ |

TABLE 6-continued

MODULATION OF NO AND/OR TNF-α

| ID | SEQUENCE | TNF-A | NO | TNF-A and NO |
|---|---|---|---|---|
| NMPF-11 | MTRV (SEQ ID NO:42) | ++++ | ++++ | ++++ |
| NMPF-12 | MTR | ++++ | ++++ | ++++ |
| NMPF-13 | LQGVLPALPQVVC (SEQ ID NO:34) | ++ | ++++ | ++++ |
| NMPF-14 | cyclic-LQGVLPALPQVVC (SEQ ID NO:34) | ++ | ++++ | ++++ |
| NMPF-43 | AQG | ++++ | ++++ | +++++++ |
| NMPF-44 | LAG | -+ | ++++ | ++++ |
| NMPF-45 | LQA | ++++ | ++++ | +++++++ |
| NMPF-46 | AQGV (SEQ ID NO:2) | ++++ | ++++ | +++++++ |
| NMPF-47 | LAGV (SEQ ID NO:26) | ++ | ++++ | ++++ |
| NMPF-48 | LQAV (SEQ ID NO:52) | ++ | ++++ | ++++ |
| NMPF-49 | LQGA (SEQ ID NO:19) | ++ | ++++ | ++++ |
| NMPF-50 | ALPALP (SEQ ID NO:21) | ++++ | ++++ | +++++++ |
| NMPF-51 | VAPALP (SEQ ID NO:22) | + | +++ | ++++ |
| NMPF-52 | VLAALP (SEQ ID NO:27) | ++ | ++++ | ++++ |
| NMPF-53 | VLPAAP (SEQ ID NO:117) | ++++ | ++++ | +++++++ |
| NMPF-54 | VLPALA (SEQ ID NO:28) | + | ++++ | ++++ |
| NMPF-55 | ALPALPQ (SEQ ID NO:23) | + | ++++ | ++++ |
| NMPF-56 | VAPALPQ (SEQ ID NO:173) | -+ | ++++ | ++++ |
| NMPF-57 | VLAALPQ (SEQ ID NO:30) | + | ++++ | ++++ |
| NMPF-58 | VLPAAPQ (SEQ ID NO:24) | ++++ | ++++ | +++++++ |
| NMPF-59 | VLPALAQ (SEQ ID NO:25) | ++ | ++++ | ++++ |
| NMPF-60 | VLPALPA (SEQ ID NO:31) | ++++ | ++++ | +++++++ |
| NMPF-61 | VVCNYRDVRFESIRLPGCP RGVNPVVSYAVALSCQCAL (SEQ ID NO:35) | -+ | ++++ | ++++ |
| NMPF-62 | VVCNYRDVRFESIRLPGCP RGVNPVVSYAVALSCQ (SEQ ID NO:169) | -+ | +++ | ++++ |
| NMPF-63 | SIRLPGCPRGVNPVVS (SEQ ID NO:39) | -+ | ++ | ++ |
| NMPF-64 | LPGCPRGVNPVVS (SEQ ID NO:40) | ++ | ++++ | ++++ |
| NMPF-65 | CPRGVNPVVS (SEQ ID NO:50) | ++ | +++ | +++ |
| NMPF-66 | LPGC (SEQ ID NO:41) | +++ | ++ | +++ |
| NMPF-67 | CPRGVNP (SEQ ID NO:170) | -+ | + | + |
| NMPF-68 | PGCP (SEQ ID NO:10) | + | + | +++ |
| NMPF-69 | RPRCRPINATLAVEKEGCP VCITVNTTICAGYCPT (SEQ ID NO:45) | -+ | ++ | ++ |
| NMPF-70 | MTRVLQGVLPALPQ (SEQ ID NO:171) | -+ | + | + |
| NMPF-71 | MTRVLPGVLPALPQVVC (SEQ ID NO:174) | -+ | -+ | -+ |
| NMPF-74 | CALCRRSTTDCGGPKDHPL TC (SEQ ID NO:46) | -+ | ++ | + |
| NMPF-75 | SKAPPPSLPSPSRLPGPS (SEQ ID NO:172) | + | ++ | ++ |
| NMPF-76 | TCDDPRFQDSSSKAPPPS LPSPSRLPGPSDTPILPQ (SEQ ID NO:48) | + | + | + |

TABLE 6-continued

MODULATION OF NO AND/OR TNF-α

| ID | SEQUENCE | TNF-A | NO | TNF-A and NO |
|---|---|---|---|---|
| NMPF-78 | CRRSTTDCGGPKDHPLTC (SEQ ID NO:47) | + | + | + | from -+ to ++++++ indicates from barely active to very active in modulating

Example V

Monkey Experiment

Efficacy of NMPF, here a mixture 1:1:1 of LQGV (SEQ ID NO:1), AQGV (SEQ ID NO:2) and VLPALP (SEQ ID NO:3), administered in a gram-negative induced rhesus monkey sepsis model for prevention of septic shock.

Overwhelming inflammatory and immune responses are essential features of septic shock and play a central part in the pathogenesis of tissue damage, multiple organ failure, and death induced by sepsis. Cytokines, especially tumor necrosis factor (TNF)-α interleukin (IL)-1β, and macrophage migration inhibitory factor (MIF), have been shown to be critical mediators of septic shock. Yet, traditional anti-TNF and anti-IL-1 therapies have not demonstrated much benefit for patients with severe sepsis. We have designed peptides that block completely LPS induced septic shock in mice, even when treatment with these peptides is started up to 24 hours after LPS injection. These peptides are also able to inhibit the production of MIF. This finding provides the possibility of therapeutic use of these peptides for the treatment of patients suffering from septic shock. Since primates are evolutionary more closer to humans, we tested these peptides for their safety and effectiveness in a primate system.

Experimental Design

| GROUP | EXPERIMENTAL TREATMENT (independent variable, e.g., placebo treated control group) | BIOTECHNIQUES | NUMBER |
|---|---|---|---|
| animal I | i.v. infusion of a lethal dose of live Escherichia. coli (10E10 CFU/kg) + antibiotics + placebo treated | Live E. coli infusion Blood sampling No recovery (section) | N = 1 |
| animal II | i.v. infusion of a lethal dose of live Escherichia. coli (10E10 CFU/kg) + antibiotics + oligopeptide (5 mg/kg of each of 3 peptides) | Live E. coli infusion Blood sampling No recovery (section) | N = 1 |

Only naive monkeys were used in this preclinical study to exclude any interaction with previous treatments. The animals were sedated with ketamine hydrochloride. Animals were intubated orally and allowed to breathe freely. The animals were kept anesthetized with $O_2/N_2O$/isoflurane. The animals received atropin as pre-medication for $O_2$/N20/isoflurane anesthesia. A level of surgical anesthesia was maintained during the 2 h infusion of E. coli and for 6 h following E. coli challenge, after which the endothracheal tubes were removed and the animals were euthanized. Before bacteria were induced, a 1 hour pre-infusion monitoring of heart-rate and blood pressure was performed.

Two rhesus monkeys were infused with a $10^{10}$CFU per kg of the Gram negative bacterium E. coli to induce a fatal septic shock. One monkey received placebo-treatment and was sacrificed within 7 hours after infusion of the bacteria without recovery from the anesthesia. The second monkey received treatment with test compound and was sacrificed at the same time point.

In a limited dose-titration experiment performed with the same bacterium strain in 1991, the used dose proved to induce fatal shock within 8 hours. In recent experiments, a 3-fold lower dose was used inducing clear clinical and pathomorphological signs of septic shock without fatal outcome.

The monkeys were kept anesthetized throughout the observation period and sacrificed 7 hours after the start of the bacterium infusion for pathological examination. The animals underwent a gross necropsy in which the abdominal and thorax cavities were opened and internal organs examined in situ.

Full Description of the Experiment with Three Rhesus Monkeys

The study was conducted in rhesus monkeys (Maccaca mulatta). Only experimentally naive monkeys were used in the study to exclude any interaction with previous treatments. Prior to the experiment, the state of health of the animals was assessed physically by a veterinarian. All animals had been declared to be in good health and were free of pathogenic ecto- and endoparasites and common bacteriological infections: Yersinia pestis, Yersinia enterocolitica, Yersinia pseudotuberculosis, Shigella, Aeromonas hydrophilia, pathogenic Campylobacter species and Salmonella.

Reagents. The Escherichia coli strain was purchased from ATCC (E. coli; 086a: K61 serotype, ATCC 33985). In a control experiment, the strain proved equally susceptible to bactericidal factors in human and rhesus monkey serum. Prior to the experiment, a fresh culture was set-up; the E. coli strain was cultured for one day, harvested and washed thoroughly to remove free endotoxine. Prior to infusion into the animal, the number and viability of the bacteria were assessed. Serial dilutions of the E. coli stock were plated on BHI agar and cultured overnight at 37° C. The colonies on each plate were counted and the number of colony-forming units per ml was calculated. The body weight measurement of the day of the experiment was used to calculate the E. coli dose and E. coli stock was suspended in isotonic saline (N.P.B.I., Emmer-Compascuum, NL) at the concentration needed for infusion (total dose volume for infusion approximately 10 ml/kg. The E. coli suspension was kept on ice until infusion.

Antibiotic was used to synchronize the shock induction in the monkeys. Baytril (Baytril 2.5%, Bayer, Del.) was used instead of gentamycin, as the strain proved only marginally susceptible to the latter antibiotic. Individual animals were identified by a number or letter combination tattooed on the chest.

Experimental design.

| GROUP (number/ letter or other identification) | EXPERIMENTAL TREATMENT (independent variable, e.g., placebo treated control group) | | NUMBER | SEX |
|---|---|---|---|---|
| Animal I | i.v. infusion of a lethal dose of live Escherichia. coli (10E10 CFU/kg) + antibiotic + placebo treated | Live E. coli infusion Blood sampling No recovery | N = 1 | F |
| Animal II | i.v. infusion of a lethal dose of live Escherichia. coli (10E10 CFU/kg) + antibiotic + NMPF-4, -6, -46; each 5 mg/kg | Live E. coli infusion Blood sampling No recovery (section) | N = 1 | F |
| Animal III | i.v. infusion of a lethal dose of live Escherichia. coli (10E10 CFU/kg) + antibiotic + NMPF-4, -6, -46; each 5 mg/kg | Live E. coli infusion Blood sampling Recovery and survival | N = 1 | F |

Anesthesia. All animals were fasted overnight prior to the experiment. On the morning of the experiment, the animals were sedated with ketamine hydrochloride (Tesink, NL) and transported to the surgery. The animal was placed on its side on a temperature-controlled heating pad to support body temperature. Rectal temperature was monitored using a Vet-OX 5700. The animals were intubated orally and were allowed to breathe freely. The animals were kept anesthesized using $O_2/N_2O$/isoflurane inhalation anesthesia during the E. coli infusion and the 7 hour observation period following E. coli challenge, after which the endothracheal tubes were removed and the animals were euthanized or allowed to recover from anesthesia. The femoral or the cephalic vein was cannulated and used for infusing isotonic saline, live E. coli and antibiotic administration. Insensible fluid loss was compensated for by infusing isotonic saline containing 2.5% glucose (Fresenius, 's Hertogenbosch, NL) at a rate of 3.3 ml/kg/hr.

Preparative actions. During anesthesia the animals were instrumented for measurement of blood pressure (with an automatic cuff), heart rate and body temperature. Isotonic saline was infused at 3.3 ml/kg/hr to compensate for fluid loss. Femoral vessels were cannulated for infusion of E. coli and antibiotics. Temperature-controlled heating pads were used to support body temperature. The monkeys were continuously monitored during the E. coli challenge and for the 6 hr period following E. coli administration. After 7 hrs, 2 animals (the control animal and one treated with NMPF) were sacrificed to compare the direct effect of the compound at the level of histology. The $3^{rd}$ animal, treated with NMPF, was allowed to recover from anesthesia and was intensively observed during the first 12 hours after recovery followed by frequent daily observation. The decision to allow the $3^{rd}$ animal to recover was made after consulting with the veterinarian.

Induction of septic shock. Before the infusion of E. coli, a 1 hr pre-infusion monitoring of heart-rate and blood pressure was performed. All three animals received an i.v. injection of E. coli 086 (k61 serotype; ATCC 33985) at a lethal dose of 10×109 CFU/kg body weight. In a dose titration study with this batch performed in 1991, this bacterial dose induced lethal shock within 8 hrs after the start of the infusion. The infusion period was 2 hrs.

Antibiotics. Baytril was administered intravenously immediately after completion of the 2 h.E. coli infusion (i.v.; dose 9 mg/kg).

Treatment with NMPF. 30 minutes post-onset of E. coli infusion, the animals were administered a single intravenous bolus injection of a mixer of NMPF oligopeptides. The oligopeptide mixer contained the following NMPF peptides: LQGV (SEQ ID NO: 1) (5 mg/kg), AQGV (SEQ ID NO:2) (5 mg/kg) and VLPALP (SEQ ID NO:3) (5 mg/kg). These NMPF peptides were dissolved in 0.9% sodium chloride for injection (N.P.B.I., Emmer Compascuum, NL).

Results

Preliminary Monkey Results

An anti-shock effect of the test compound on sepsis in the monkey treated with the oligopeptide mixture, namely the inhibition of the effect of the sepsis in this early 7-hour trajectory of this primate model, was observed. Immunomodulatory effects with these peptides have been observed in vitro/ex vivo such as in T-cell assays, the inhibition of pathological Th1 immune responses, suppression of inflammatory cytokines (MIF), increase in production of anti-inflammatory cytokines (IL-10, TGF-beta) and immunomodulatory effects on antigen-presenting cells (APC) like dendritic cells and macrophages.

The following organs were weighed and a bacterial count was performed: kidneys, liver, lungs, lymph nodes, and gross lesions.

Tissues of all organs were preserved in neutral aqueous phosphate buffered 4% solution of formaldehyde. Lymphoid organs were cryopreserved. All tissues will be processed for histopathological examination.

Further Results Obtained in the Three-monkey Experiment

Monkey 429(control). Female monkey (5.66 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. Baytril was administered intravenously immediately after completion of the 2 h. E. coli infusion (i.v.; dose 9 mg/kg). After the E. coli injection, the monkey was observed by the authorized veterinarian without knowing which of the monkeys received NMPF treatment. The clinical observations were as follows: vomiting, undetectable pulse, heart arythmia, abnormalities in ECG: signs of ventricle dilatation/heart decompensation (prolonged QRS complex, extra systoles), decreased blood clotting and forced respiration. In addition, there was big fluctuation in heart rate (30-150 beats per minute), collapse of both systolic and diastolic blood pressure (35/20 mmHg) and decrease in blood oxygen concentration (80-70%). Seven hours after the start of the E. coli infusion, monkey began to vomit blood and feces, and have convulsions. After final examination, the veterinarian did not give permission to let this monkey awake. At this time point, the control monkey was euthanized. Hereafter, post-mortem examination was conducted and internal organs were examined in situ. A number of internal bleedings were found by the pathologist.

Monkey 459(NMPF). Female monkey (5.44 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. Thirty minutes after the initiation of E. coli infusion, NMPF was i.v. injected in a single bolus injection. Baytril was administered intravenously immediately after completion of the 2 h. E. coli infusion (i.v.; dose 9 mg/kg). After the E. coli injection, this monkey was also observed by the authorized veterinarian without knowing which of the monkeys received NMPF treatment. The clinical observations were as follows: normal pulse, heart sounds normal, normal ECG, higher heart-rate but otherwise stable (180 beats per minute), no hypotension (75/30 mmHg), normal blood oxygen concentration (95-85%), lungs sound normal, normal turgor. Seven hours after the start of the E. coli infusion, the clinical condition of the monkey was stable. After final examination, the veterinarian did give permission to let this monkey awake due to her stable condition. In order to compare the hematological and immunological parameters between the control and NMPF-treated monkey, at this time point the NMPF-treated monkey 459 was euthanized. Hereafter, post-mortem examination was conducted and internal organs were examined in situ. No macroscopic internal bleedings were found by the pathologist.

Monkey 427(NMPF). Female monkey (4.84 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. Thirty minutes after the initiation of E. coli infusion, NMPF was i.v. injected. Baytril was administered intravenously immediately after completion of the 2 h. E. coli infusion (i.v.; dose 9 mg/kg). After the E. coli injection, this monkey was also observed by the authorized veterinarian doctor without knowing which of the monkeys received NMPF treatment. The clinical observations were as follows: normal pulse, heart sounds normal, normal ECG, moderately higher heart-rate but otherwise stable (160 beats per minute), no hypotension (70/30 mmHg), normal blood oxygen concentration (95-90%), lungs sound normal, normal turgor. Seven hours after the start of the E. coli infusion, the clinical condition of the monkey was stable. After final examination, the veterinarian did give permission to let this monkey wake up due to her stable condition. The monkey woke up quickly, she was alert and there was a slow disappearance of oedema.

What is claimed is:

1. A composition comprising one or more purified or isolated peptides of the sequence AQGV (SEQ ID NO:2).

* * * * *

```
                           SEQUENCE LISTING

<160> NUMBER OF SEQ ID NOS: 175

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 1

Leu Gln Gly Val
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 2

Ala Gln Gly Val
1

<210> SEQ ID NO 3
<211> LENGTH: 6
<212> TYPE: PRT
<213> ORGANISM: Artificial Sequence
```

```
<220> FEATURE:
<223> OTHER INFORMATION: Description of Artificial Sequence:
      oligopeptide

<400> SEQUENCE: 3

Val Leu Pro Ala Leu Pro
 1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:
      swiss/p36507/MPK2 Human

<400> SEQUENCE: 4

Met Leu Ala Arg Arg Lys Pro Val Leu Pro Ala Leu Thr Ile Asn Pro
 1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:
      swiss/p36507/MPK2 Human

<400> SEQUENCE: 5

Met Leu Ala Arg Arg Lys Pro
 1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:
      swiss/p36507/MPK2 Human

<400> SEQUENCE: 6

Met Leu Ala Arg
 1

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      swiss/p36507/MPK2 Human

<400> SEQUENCE: 7

Val Leu Pro Ala Leu Thr
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:
      pdb/1QMH/1QMH-A

<400> SEQUENCE: 8

Val Leu Pro Ala Leu
 1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      pdb/4NOS/4NOS-A

<400> SEQUENCE: 9

Phe Pro Gly Cys
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
      Hs.297775.1

<400> SEQUENCE: 10

Pro Gly Cys Pro
  1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:
      swiss/P81272/NS2B HUMAN

<400> SEQUENCE: 11

Gly Val Leu Pro Ala Val Pro
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:
      swiss/P81272/NS2B HUMAN

<400> SEQUENCE: 12

Val Leu Pro Ala Val Pro
  1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:
      pdb/1FZV/1FZV-A

<400> SEQUENCE: 13

Pro Ala Val Pro
  1

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:
      oligopeptide
```

```
<400> SEQUENCE: 14

Leu Gln Gly Val Val Pro Arg Gly Val
  1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 15

Gly Val Val Pro
  1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      oligopeptide

<400> SEQUENCE: 16

Val Pro Arg Gly Val
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 17

Pro Arg Gly Val
  1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:
      polypeptide

<400> SEQUENCE: 18

Met Ala Pro Lys Lys
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 19

Leu Gln Gly Ala
  1
```

```
<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:
      oligopeptide

<400> SEQUENCE: 20

Val Leu Pro Ala Leu Pro Gln Val Val Cys
 1               5                  10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 21

Ala Leu Pro Ala Leu Pro
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 22

Val Ala Pro Ala Leu Pro
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 23

Ala Leu Pro Ala Leu Pro Gln
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 24

Val Leu Pro Ala Ala Pro Gln
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:
      oligopeptide
```

```
<400> SEQUENCE: 25

Val Leu Pro Ala Leu Ala Gln
 1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 26

Leu Ala Gly Val
 1

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 27

Val Leu Ala Ala Leu Pro
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 28

Val Leu Pro Ala Leu Ala
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 29

Val Leu Pro Ala Leu Pro Gln
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 30

Val Leu Ala Ala Leu Pro Gln
 1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 31

Val Leu Pro Ala Leu Pro Ala
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 32

Gly Val Leu Pro Ala Leu Pro
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:
      oligopeptide

<400> SEQUENCE: 33

Gly Val Leu Pro Ala Leu Pro Gln
  1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:
      oligopeptide

<400> SEQUENCE: 34

Leu Gln Gly Val Leu Pro Ala Leu Pro Gln Val Val Cys
  1               5                  10

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence:
      oligopeptide

<400> SEQUENCE: 35

Val Val Cys Asn Tyr Arg Asp Val Arg Phe Glu Ser Ile Arg Leu Pro
  1               5                  10                  15

Gly Cys Pro Arg Gly Val Asn Pro Val Val Ser Tyr Ala Val Ala Leu
             20                  25                  30

Ser Cys Gln Cys Ala Leu
         35
```

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:
      oligopeptide

<400> SEQUENCE: 36

Arg Pro Arg Cys Arg Pro Ile Asn Ala Thr Leu Ala Val Glu Lys
 1               5                  10                  15

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence:
      oligopeptide

<400> SEQUENCE: 37

Glu Gly Cys Pro Val Cys Ile Thr Val Asn Thr Thr Ile Cys Ala Gly
 1               5                  10                  15

Tyr Cys Pro Thr
            20

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence:
      oligopeptide

<400> SEQUENCE: 38

Ser Lys Ala Pro Pro Pro Ser Leu Pro Ser Pro Ser Arg Leu Pro Gly
 1               5                  10                  15

Pro Ser

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:
      oligopeptide

<400> SEQUENCE: 39

Ser Ile Arg Leu Pro Gly Cys Pro Arg Gly Val Asn Pro Val Val Ser
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:
      oligopeptide

<400> SEQUENCE: 40

Leu Pro Gly Cys Pro Arg Gly Val Asn Pro Val Val Ser
 1               5                  10

<210> SEQ ID NO 41
<211> LENGTH: 4
<212> TYPE: PRT
<213> ORGANISM: Artificial Sequence
```

```
<220> FEATURE:
<223> OTHER INFORMATION: Description of Artificial Sequence:
      oligopeptide

<400> SEQUENCE: 41

Leu Pro Gly Cys
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 42

Met Thr Arg Val
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 43

Gln Val Val Cys
  1

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 44

Met Thr Arg Val Leu Gln Gly Val Leu Pro Ala Leu Pro Gln Val Val
  1               5                  10                  15

Cys

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 45

Arg Pro Arg Cys Arg Pro Ile Asn Ala Thr Leu Ala Val Glu Lys Glu
  1               5                  10                  15

Gly Cys Pro Val Cys Ile Thr Val Asn Thr Thr Ile Cys Ala Gly Tyr
               20                  25                  30

Cys Pro Thr
           35

<210> SEQ ID NO 46
<211> LENGTH: 21
<212> TYPE: PRT
<213> ORGANISM: Artificial Sequence
```

-continued

```
<220> FEATURE:
<223> OTHER INFORMATION: Description of Artificial Sequence: peptide
      signalling molecule

<400> SEQUENCE: 46

Cys Ala Leu Cys Arg Arg Ser Thr Thr Asp Cys Gly Gly Pro Lys Asp
 1               5                  10                  15

His Pro Leu Thr Cys
             20

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 47

Cys Arg Arg Ser Thr Thr Asp Cys Gly Gly Pro Lys Asp His Pro Leu
 1               5                  10                  15

Thr Cys

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 48

Thr Cys Asp Asp Pro Arg Phe Gln Asp Ser Ser Ser Ser Lys Ala Pro
 1               5                  10                  15

Pro Pro Ser Leu Pro Ser Pro Ser Arg Leu Pro Gly Pro Ser Asp Thr
             20                  25                  30

Pro Ile Leu Pro Gln
         35

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 49

Leu Gln Gly Val Leu Pro Ala Leu Pro Gln
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: NMPF
      peptide

<400> SEQUENCE: 50

Cys Pro Arg Gly Val Asn Pro Val Val Ser
 1               5                  10
```

-continued

```
<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: probe to
      represent the NF-kappaB binding sequence

<400> SEQUENCE: 51
agctcagagg gggactttcc gagag                                              25

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: peptide
      LQAV showed smaller infarcted area

<400> SEQUENCE: 52

Leu Gln Ala Val
  1

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:
      pdb/1DE7/1DE7-A

<400> SEQUENCE: 53

Leu Gln Gly Val Val
  1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence:
      pdb/1DE7/1DE7-A

<400> SEQUENCE: 54

Leu Gln Gly Val Val Pro
  1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:
      pdb/1DL6/1DL6-A

<400> SEQUENCE: 55

Leu Asp Ala Leu Pro
  1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:
      pdb/1QMH/1QMH-A
```

```
<400> SEQUENCE: 56

Leu Gln Thr Val
 1

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence:
      pdb/1QMH/1QMH-A

<400> SEQUENCE: 57

Leu Val Leu Gln Thr Val Leu Pro Ala Leu
 1               5                  10

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 58

Ile Gln Gly Leu
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 59

Leu Pro Lys Leu
 1

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 60

Leu Leu Pro Lys Leu
 1               5

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence:
      pdb/1B9O/1B9O-A

<400> SEQUENCE: 61

Leu Pro Glu Leu
 1
```

```
<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:
      pdb/1GLU/1GLU-A

<400> SEQUENCE: 62

Pro Ala Arg Pro
  1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence:
      pdb/2KIN/2KIN-B

<400> SEQUENCE: 63

Met Thr Arg Ile
  1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 64

Leu Gln Lys Leu
  1

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 65

Leu Gln Lys Leu Leu
  1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 66

Pro Glu Ala Pro
  1

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      pdb/1SMP/1SMP-I
```

```
<400> SEQUENCE: 67

Leu Gln Lys Leu Leu Pro Glu Ala Pro
 1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence:
      pdb/1ES/1ES7-B

<400> SEQUENCE: 68

Pro Thr Leu Pro
 1

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence:
      pdb/1ES/1ES7-B

<400> SEQUENCE: 69

Leu Gln Pro Thr Leu
 1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence:
      pdb/1BHX/1BHX-F

<400> SEQUENCE: 70

Leu Gln Val Val
 1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence:
      pdb/1VCB/1VCB-A

<400> SEQUENCE: 71

Pro Glu Leu Pro
 1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 72

Pro Ala Ala Pro
 1
```

```
<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 73

Pro Ala Ala Pro Gln
 1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 74

Pro Ala Ala Pro Gln Val
 1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 75

Leu Pro Ala Leu
 1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 76

Pro Ala Leu Pro
 1

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 77

Pro Ala Leu Pro Glu
 1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence:
      pdb/1R2A/1R2A-A
```

```
<400> SEQUENCE: 78

Leu Thr Glu Leu Leu
  1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: C3G peptide

<400> SEQUENCE: 79

Pro Pro Pro Ala Leu Pro Pro Lys Lys Arg
  1               5                  10

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence:
      pdb/1RLQ/1RLQ-R

<400> SEQUENCE: 80

Leu Pro Pro Leu
  1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence:
      pdb/1RLQ/1RLQ-R; swissnew/P01229/LSHB_HUMAN

<400> SEQUENCE: 81

Pro Pro Leu Pro
  1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence:
      pdb/1TNT/1TNT

<400> SEQUENCE: 82

Leu Pro Gly Leu
  1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence:
      pdb/1GJS/1GJS-A

<400> SEQUENCE: 83

Leu Ala Ala Leu
  1

<210> SEQ ID NO 84
<211> LENGTH: 5
<212> TYPE: PRT
<213> ORGANISM: Artificial Sequence
```

```
<220> FEATURE:
<223> OTHER INFORMATION: Description of Artificial Sequence:
      pdb/1GJS/1GJS-A

<400> SEQUENCE: 84

Leu Ala Ala Leu Pro
 1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence:
      pdb/1GBR/1GBR-B

<400> SEQUENCE: 85

Pro Lys Leu Pro
 1

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence:
      pdb/1A78/1A78-A

<400> SEQUENCE: 86

Val Leu Pro Ser Ile Pro
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence:
      pdb/1FZV/1FZV-A

<400> SEQUENCE: 87

Met Leu Pro Ala Val Pro
 1               5

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence:
      pdb/1JLI/1JLI

<400> SEQUENCE: 88

Leu Pro Cys Leu
 1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence:
      pdb/1JLI/1JLI

<400> SEQUENCE: 89

Pro Cys Leu Pro
 1
```

```
<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence:
      pdb/1HSS/1HSS-A

<400> SEQUENCE: 90

Val Pro Ala Leu Pro
 1               5

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence:
      pdb/1PRX/1PRX-A

<400> SEQUENCE: 91

Pro Thr Ile Pro
 1

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence:
      pdb/1PRX/1PRX-A

<400> SEQUENCE: 92

Val Leu Pro Thr Ile Pro
 1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence:
      pdb/1RCY/1RCY

<400> SEQUENCE: 93

Val Leu Pro Gly Phe Pro
 1               5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence:
      pdb/1A3Z/1A3Z

<400> SEQUENCE: 94

Pro Gly Phe Pro
 1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence:
      pdb/1GER/1GER-A
```

-continued

```
<400> SEQUENCE: 95

Leu Pro Ala Leu Pro
  1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence:
      pdb/1BBS/1BBS

<400> SEQUENCE: 96

Met Pro Ala Leu Pro
  1               5

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: AI188872
<220> FEATURE:
<221> NAME/KEY: MISC_FEATURE
<222> LOCATION: (2)
<223> OTHER INFORMATION: The Xaa at position 2 may be any amino acid

<400> SEQUENCE: 97

Met Xaa Arg Val Leu Gln Gly Val Leu Pro Ala Leu Pro Gln Val Val
  1               5                  10                  15

Cys

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: AI188872
<220> FEATURE:
<221> NAME/KEY: MISC_FEATURE
<222> LOCATION: (2)
<223> OTHER INFORMATION: The Xaa at position 2 may be any amino acid

<400> SEQUENCE: 98

Met Xaa Arg Val
  1

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: AI126906

<400> SEQUENCE: 99

Ile Thr Arg Val Met Gln Gly Val Ile Pro Ala Leu Pro Gln Val Val
  1               5                  10                  15

Cys

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: AI221581
```

```
<400> SEQUENCE: 100

Met Thr Arg Val Leu Gln Val Val Leu Leu Ala Leu Pro Gln Leu Val
  1               5                  10                  15

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Mm.42246.3

<400> SEQUENCE: 101

Lys Val Ile Gln Gly Ser Leu Asp Ser Leu Pro Gln Ala Val
  1               5                  10

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Mm.42246.3

<400> SEQUENCE: 102

Leu Asp Ser Leu
  1

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Mm.22430.1

<400> SEQUENCE: 103

Val Leu Gln Ala Ile Leu Pro Ser Ala Pro Gln
  1               5                  10

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Mm.22430.1

<400> SEQUENCE: 104

Leu Gln Ala Ile Leu
  1               5

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Mm.22430.1

<400> SEQUENCE: 105

Pro Ser Ala Pro
  1

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Hs.63758.4
```

-continued

```
<400> SEQUENCE: 106

Lys Val Leu Gln Gly Arg Leu Pro Ala Val Ala Gln Ala Val
 1               5                  10

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Hs.63758.4

<400> SEQUENCE: 107

Leu Pro Ala Val
 1

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Mm.129320.2

<400> SEQUENCE: 108

Leu Val Gln Lys Val Val Pro Met Leu Pro Arg Leu Leu Cys
 1               5                  10

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Mm.129320.2

<400> SEQUENCE: 109

Leu Pro Arg Leu
 1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Mm.129320.2

<400> SEQUENCE: 110

Pro Met Leu Pro
 1

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Mm.22430.1

<400> SEQUENCE: 111

Pro Ser Ala Pro Gln
 1               5

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: P20155
```

```
<400> SEQUENCE: 112

Leu Pro Gly Cys Pro Arg His Phe Asn Pro Val
  1               5                  10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Rn.2337.1

<400> SEQUENCE: 113

Leu Val Gly Cys Pro Arg Asp Tyr Asp Pro Val
  1               5                  10

<210> SEQ ID NO 114
<211> LENGTH: 4
<212> TYPE: PRT
<213> ORGANISM: Artificial Sequence
<220> FEATURE:
<223> OTHER INFORMATION: Description of Artificial Sequence: Rn.2337.1

<400> SEQUENCE: 114

Leu Val Gly Cys
  1

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Hs.297775.1

<400> SEQUENCE: 115

Pro Gly Cys Pro Arg Gly
  1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Mm.1359.1

<400> SEQUENCE: 116

Leu Pro Gly Cys Pro
  1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence:
      sptrembl/O56177/O56177

<400> SEQUENCE: 117

Val Leu Pro Ala Ala Pro
  1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence:
      sptrembl/Q9W234/Q9W234
```

```
<400> SEQUENCE: 118

Leu Ala Gly Thr Ile Pro Ala Thr Pro
 1               5

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9W234/Q9W234

<400> SEQUENCE: 119

Pro Ala Thr Pro
 1

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence:
      sptrembl/Q9IYZ3/Q9IYZ3

<400> SEQUENCE: 120

Gly Leu Leu Pro Cys Leu Pro
 1               5

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 121

Pro Gly Ala Pro
 1

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 122

Leu Pro Gln Arg Pro Arg Gly Pro Asn Pro
 1               5                   10

<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 123

Pro Arg Gly Pro
 1
```

```
<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Hs.303116.2

<400> SEQUENCE: 124

Gly Cys Pro Arg
  1

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence:
      pdb/1DU3/1DU3-A

<400> SEQUENCE: 125

Gly Cys Pro Arg Gly Met
  1               5

<210> SEQ ID NO 126
<211> LENGTH: 4
<212> TYPE: PRT
<213> ORGANISM: Artificial Sequence
<220> FEATURE:
<223> OTHER INFORMATION: Description of Artificial Sequence:
      pdb/1BIO/1BIO

<400> SEQUENCE: 126

Leu Gln His Val
  1

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence:
      pdb/1FL7/1FL7-B

<400> SEQUENCE: 127

Val Pro Gly Cys
  1

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence:
      pdb/1HR6/1HR6-A

<400> SEQUENCE: 128

Cys Pro Arg Gly
  1

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence:
      pdb/1H6/1HR6-A
```

```
<400> SEQUENCE: 129

Leu Lys Gly Cys
  1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 130

Pro Pro Gly Pro
  1

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 131

Leu Pro Gly Cys Pro Arg Glu Val
  1               5

<210> SEQ ID NO 132
<211> LENGTH: 4
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 132

Cys Pro Arg Glu
  1

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 133

Met Met Arg Val Leu Gln Ala Val Leu Pro Pro Leu Pro Gln Val Val
  1               5                  10                  15

Cys

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 134

Met Met Arg Val
  1
```

```
<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 135

Val Leu Pro Pro Leu Pro
  1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 136

Val Leu Pro Pro Leu Pro Gln
  1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 137

Ala Val Leu Pro Pro Leu Pro
  1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 138

Ala Val Leu Pro Pro Leu Pro Gln
  1               5

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 139

Met Met Arg Val Leu Gln Ala Val Leu Pro Pro Val Pro Gln Val Val
  1               5                  10                  15

Cys

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence:
      swissnew/P07434/CGHB PAPAN
```

```
<400> SEQUENCE: 140

Leu Gln Ala Gly
  1

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 141

Val Leu Pro Pro Val Pro
  1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 142

Val Leu Pro Pro Val Pro Gln
  1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 143

Ala Val Leu Pro Pro Val Pro
  1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 144

Ala Val Leu Pro Pro Val Pro Gln
  1               5

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 145

Met Thr Arg Asp
  1
```

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 146

Gln Asp Val Cys
 1

<210> SEQ ID NO 147
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 147

Ile Pro Gly Cys
 1

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence:
      sptrembl/Q9Z284/Q9Z284

<400> SEQUENCE: 148

Pro Ala Leu Pro Ser
 1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

<400> SEQUENCE: 149

Leu Pro Gly Gly Pro Arg
 1               5

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

<400> SEQUENCE: 150

Leu Pro Gly Gly
 1

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

```
<400> SEQUENCE: 151

Gly Gly Pro Arg
 1

<210> SEQ ID NO 152
<211> LENGTH: 4
<212> TYPE: PRT
<213> ORGANISM: Artificial Sequence
<220> FEATURE:
<223> OTHER INFORMATION: Description of Artificial Sequence: XP_028754

<400> SEQUENCE: 152

Leu Gln Arg Gly
 1

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: XP_028754

<400> SEQUENCE: 153

Leu Gln Arg Gly Val
 1               5

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: XP_028754

<400> SEQUENCE: 154

Leu Gly Gln Leu
 1

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: SignalP
      (CBS)

<400> SEQUENCE: 155

Met Thr Arg Val Leu Gln Gly Val Leu Pro Ala Leu Pro
 1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 156

Val Leu Gln Gly Val Leu Pro Ala Leu
 1               5

<210> SEQ ID NO 157
<211> LENGTH: 9
<212> TYPE: PRT
<213> ORGANISM: Artificial Sequence
```

```
<220> FEATURE:
<223> OTHER INFORMATION: Description of Artificial Sequence: HLA
      molecule type I (A_0201)

<400> SEQUENCE: 157

Gly Val Leu Pro Ala Leu Pro Gln Val
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 158

Val Leu Pro Ala Leu Pro Gln Val Val
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 159

Arg Leu Pro Gly Cys Pro Arg Gly Val
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 160

Thr Met Thr Arg Val Leu Gln Gly Val
1               5

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: MHC II
      (H2-Ak15-mers)

<400> SEQUENCE: 161

Cys Pro Thr Met Thr Arg Val Leu Gln Gly Val Leu Pro Ala Leu
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: MHC II
      (H2-Ak15-mers)

<400> SEQUENCE: 162

Pro Gly Cys Pro Arg Gly Val Asn Pro Val Val Ser Tyr Ala Val
1               5                   10                  15
```

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*010115-mers

<400> SEQUENCE: 163

Pro Arg Gly Val Asn Pro Val Val Ser Tyr Ala Val Ala Leu Ser
 1               5                  10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*010115-mers

<400> SEQUENCE: 164

Thr Arg Val Leu Gln Gly Val Leu Pro Ala Leu Pro Gln Val Val
 1               5                  10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*010115-mers

<400> SEQUENCE: 165

Leu Gln Gly Val Leu Pro Ala Leu Pro Gln Val Val Cys Asn Tyr
 1               5                  10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0301 (DR17) 15-mers

<400> SEQUENCE: 166

Met Thr Arg Val Leu Gln Gly Val Leu Pro Ala Leu Pro Gln Val
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0301 (DR17) 15-mers

<400> SEQUENCE: 167

Ser Ile Arg Leu Pro Gly Cys Pro Arg Gly Val Asn Pro Val Val
 1               5                  10                  15

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: NMPF-56
      peptide -continued

```
<400> SEQUENCE: 168

Val Ala Pro Ala Leu Pro Gln
  1               5

<210> SEQ ID NO 169
<211> LENGTH: 35
<212> TYPE: PRT
<213> ORGANISM: Artificial Sequence
<220> FEATURE:
<223> OTHER INFORMATION: Description of Artificial Sequence: NMPF-62
      peptide

<400> SEQUENCE: 169

Val Val Cys Asn Tyr Arg Asp Val Arg Phe Glu Ser Ile Arg Leu Pro
  1               5                  10                  15

Gly Cys Pro Arg Gly Val Asn Pro Val Val Ser Tyr Ala Val Ala Leu
             20                  25                  30

Ser Cys Gln
         35

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: NMPF-67
      peptide

<400> SEQUENCE: 170

Cys Pro Arg Gly Val Asn Pro
  1               5

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: NMPF-70
      peptide

<400> SEQUENCE: 171

Met Thr Arg Val Leu Gln Gly Val Leu Pro Ala Leu Pro Gln
  1               5                  10

<210> SEQ ID NO 172
<211> LENGTH: 18
<212> TYPE: PRT
<213> ORGANISM: Artificial Sequence
<220> FEATURE:
<223> OTHER INFORMATION: Description of Artificial Sequence: NMPF-75
      peptide

<400> SEQUENCE: 172

Ser Lys Ala Pro Pro Pro Ser Leu Pro Ser Pro Ser Arg Leu Pro Gly
  1               5                  10                  15

Pro Cys

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: NMPF-56
      peptide
```

```
<400> SEQUENCE: 173

Val Ala Pro Ala Leu Pro Gln
 1               5

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: NMPF-71
      peptide

<400> SEQUENCE: 174

Met Thr Arg Val Leu Pro Gly Val Leu Pro Ala Leu Pro Gln Val Val
 1               5                  10                  15

Cys

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: NMPF
      peptide

<400> SEQUENCE: 175

Cys Arg Gly Val Asn Pro Val Val Ser
 1               5
```